(12) United States Patent
Keast

(10) Patent No.: US 10,336,497 B2
(45) Date of Patent: Jul. 2, 2019

(54) CORE TRAY

(71) Applicant: Prospectors IP Holdings Pty Limited, Bella Vista, New South Wales (AU)

(72) Inventor: Robert Mark Keast, Bella Vista (AU)

(73) Assignee: Prospectors IP Holdings Pty Limited, Bella Vista NSW (AU)

( * ) Notice: Subject to any disclaimer, the term of this patent is extended or adjusted under 35 U.S.C. 154(b) by 0 days.

(21) Appl. No.: 14/387,300

(22) PCT Filed: Mar. 26, 2013

(86) PCT No.: PCT/AU2013/000304
§ 371 (c)(1),
(2) Date: Sep. 23, 2014

(87) PCT Pub. No.: WO2013/142899
PCT Pub. Date: Oct. 3, 2013

(65) Prior Publication Data
US 2016/0059987 A1    Mar. 3, 2016

(30) Foreign Application Priority Data

Mar. 26, 2012 (AU) ................................ 2012901218
Jul. 23, 2012 (AU) ................................ 2012903134

(51) Int. Cl.
*B65D 1/36* (2006.01)
*B65D 25/28* (2006.01)
(Continued)

(52) U.S. Cl.
CPC ............... *B65D 1/36* (2013.01); *B65D 25/28* (2013.01); *B65D 25/2888* (2013.01);
(Continued)

(58) Field of Classification Search
CPC ........ B65D 1/34; B65D 1/36; B65D 25/2897; B65D 25/30; B65D 71/0003; B65D 85/20; E21B 25/005
(Continued)

(56) References Cited

U.S. PATENT DOCUMENTS 3,363,802 A * 1/1968 Cornelius .......... B65D 71/0003
                                                    206/203
3,467,247 A * 9/1969 Weiss ....................... B65D 1/36
                                                    206/561
(Continued)

FOREIGN PATENT DOCUMENTS

AU    2004100505 A4 * 7/2004
AU    2009222632 A1 * 4/2010 ............... B65D 1/36
(Continued)

OTHER PUBLICATIONS https://www.youtube.com/watch?v=pjGn5bs8AcU, Published on Jan. 13, 2011 by DiscovererCoreTray (Year: 2011).*
(Continued)

*Primary Examiner* — Mollie Impink
(74) *Attorney, Agent, or Firm* — Cooper & Dunham LLP

(57) ABSTRACT

A core tray is provided, comprising a body including at least one channel arranged to hold at least one core sample, wherein the body includes at least one set of handles arranged to, in use, allow a user to grip the core tray to assist in moving the core tray.

14 Claims, 40 Drawing Sheets

(51) Int. Cl.
   *B65D 85/20* (2006.01)
   *E21B 25/00* (2006.01)
   *B65D 85/00* (2006.01)
   *G01N 33/24* (2006.01)

(52) U.S. Cl.
   CPC ......... *B65D 25/2897* (2013.01); *B65D 85/20* (2013.01); *B65D 85/70* (2013.01); *E21B 25/00* (2013.01); *E21B 25/005* (2013.01); *B65D 2501/24522* (2013.01); *B65D 2501/24535* (2013.01); *B65D 2501/24554* (2013.01); *B65D 2501/24796* (2013.01); *B65D 2501/24878* (2013.01); *B65D 2519/00791* (2013.01); *G01N 33/24* (2013.01)

(58) Field of Classification Search
   USPC ........................................................ 206/443
   See application file for complete search history.

(56) References Cited

U.S. PATENT DOCUMENTS

| | | | | |
|---|---|---|---|---|
| 3,707,227 A | * | 12/1972 | Britt | ............ B01L 9/06 206/443 |
| 3,759,375 A | * | 9/1973 | Nappi | ............ A45D 40/0087 132/286 |
| 3,782,582 A | * | 1/1974 | Lybbert | ............ B65D 1/36 206/503 |
| 3,786,932 A | | 1/1974 | Smith | |
| 3,791,549 A | * | 2/1974 | Delbrouck | ............ B65D 71/70 206/509 |
| 3,910,410 A | * | 10/1975 | Shaw | ............ B65D 75/26 206/306 |
| 4,364,477 A | * | 12/1982 | Stromberg | ............ B65D 25/30 206/511 |
| 4,792,045 A | * | 12/1988 | Creaden | ............ B65D 1/36 206/419 |
| 4,874,091 A | * | 10/1989 | McEwen | ............ B65D 85/24 206/443 |
| 4,971,275 A | * | 11/1990 | Roberts | ............ B63C 11/02 248/152 |
| D424,941 S | * | 5/2000 | Boutour | ............ D9/456 |
| 2006/0109105 A1 | * | 5/2006 | Varner | ............ G06Q 10/08 340/539.12 |
| 2008/0116099 A1 | * | 5/2008 | Garcia | ............ B65D 1/36 206/503 |
| 2010/0018886 A1 | | 1/2010 | Wilson | |

FOREIGN PATENT DOCUMENTS

CA    972302    8/1975
WO    96/37410    11/1996

OTHER PUBLICATIONS

International Search Report Issued for PCT/AU2013/000304 dated Apr. 30, 2013.

* cited by examiner

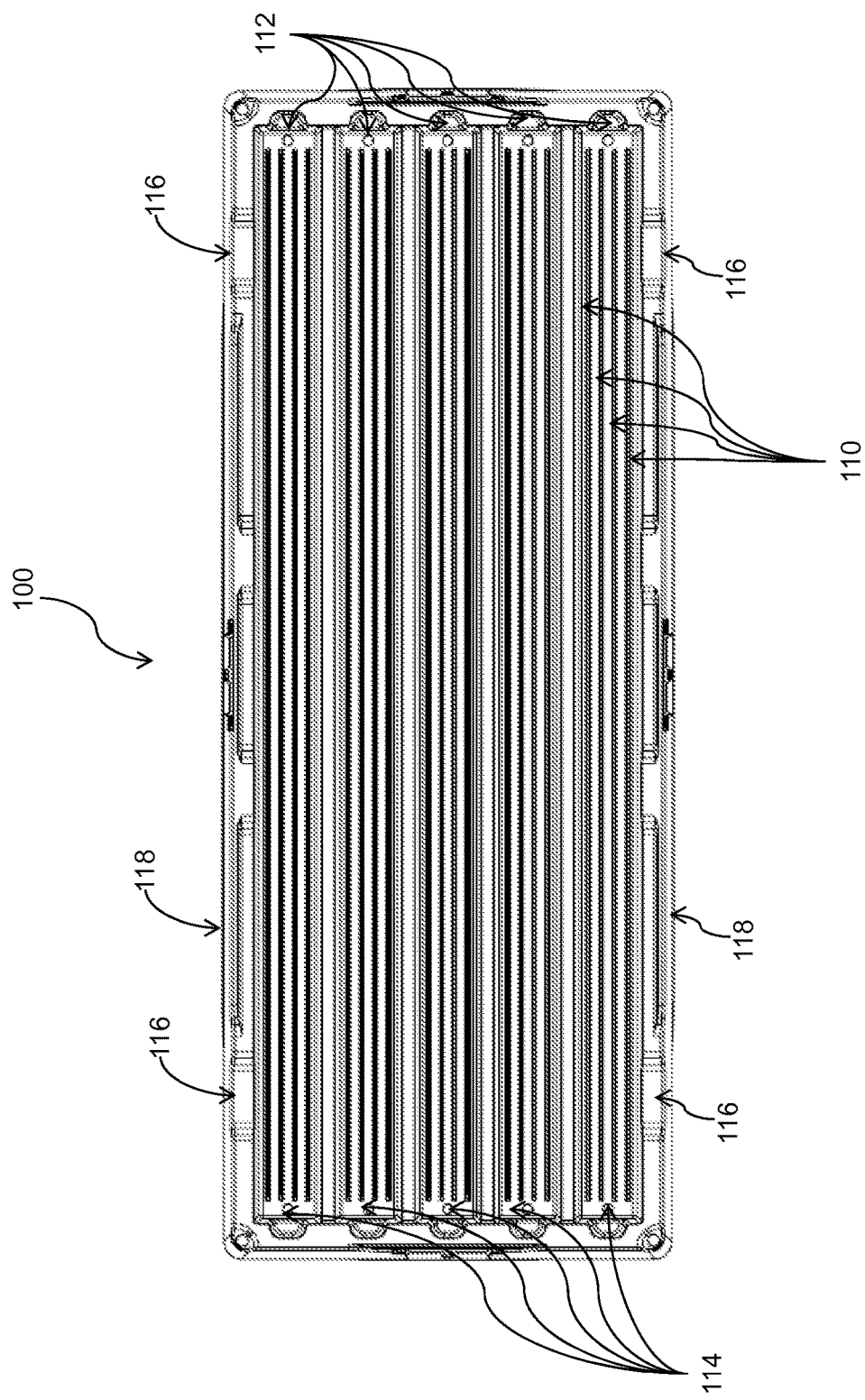

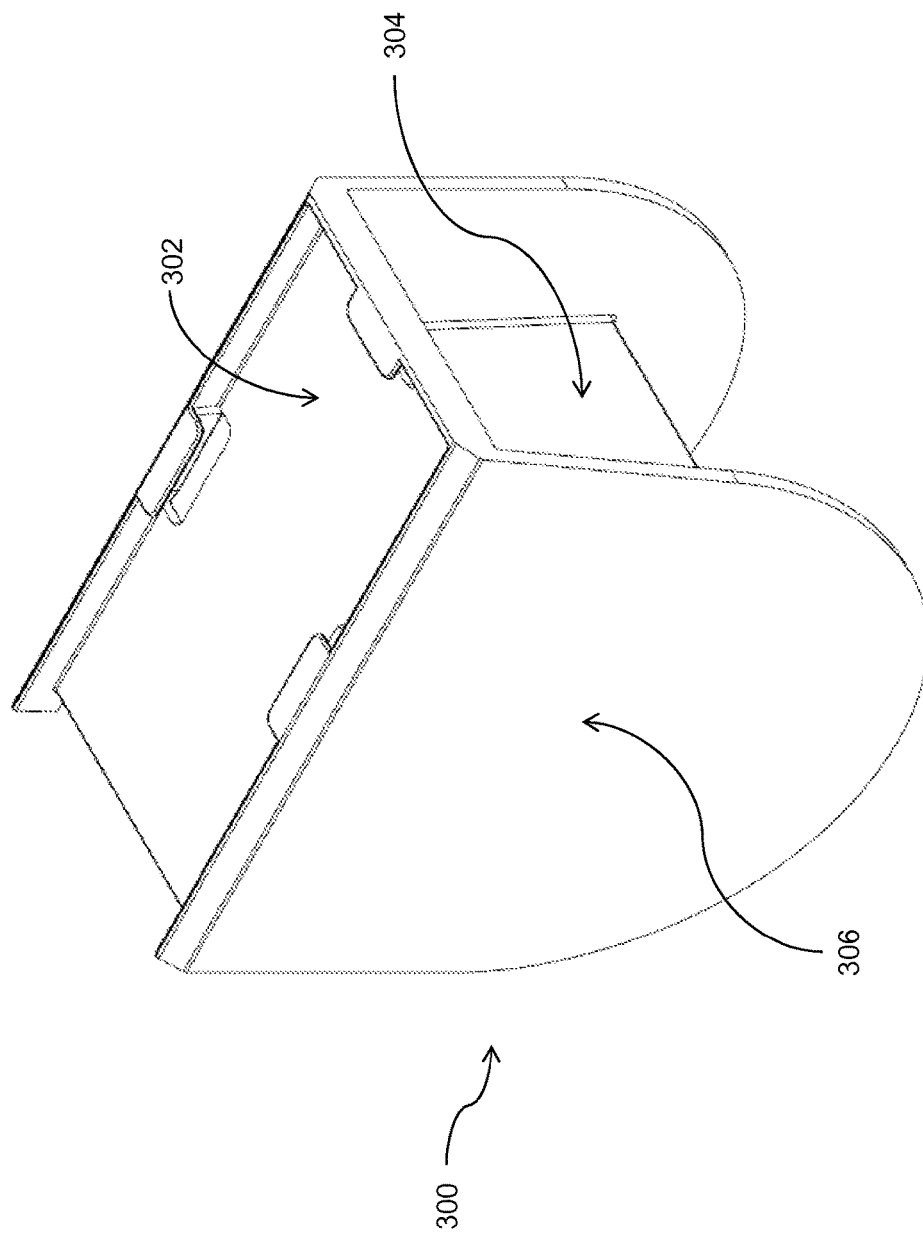

CORE TRAY

TECHNICAL FIELD

The present invention relates to a core tray. Embodiments of the invention find particular, but not exclusive, use in the housing, organisation, transport, cataloguing and storage of core samples.

BACKGROUND OF THE INVENTION

A core sample is a cylindrical section of a substance. Most core samples are obtained by drilling with a hollow steel tube drill (commonly referred to as a core drill) into the substance. Generally, the substance is sediment or rock, although core samples may be taken from man-made substances, such as concrete, ceramic material, or metal. Some medical procedures also use core drills to collect samples of bone.

The drilling and collection of core samples is quite common in the mining industry, where geologists take core samples at different geographical sites to later analyse for mineral or metal content.

When core samples are taken, there is a need to house, organise, transport, catalogue and store the samples. It has been known to use "core trays" (sometimes referred to as "core boxes") to house, organise, transport, catalogue and store the samples. Core trays are, as the name implies, a tray-like device with a number of elongate slots or channels, each channel being arranged to hold a portion of a core sample.

Generally, such trays are constructed from a wooden, metal or plastic material. The choice of material, in the past, has been largely determined by local resources and skills. For example, in Canada, core trays are commonly made from wood, as wood is generally in abundant supply near the areas where mineral or mining exploration occurs.

In Australia, however, core trays have generally been made from metal (and more recently from plastic).

There is generally no set standard for core trays, other than the requirement to size the channels so that core samples can fit into the channels. The length and width of the trays are generally a function of local requirements. It is quite common for different companies and/or mine sites to have different tray size requirements.

The preceding discussion of the background art is intended to facilitate an understanding of the present invention only. The discussion is not an acknowledgement or admission that any of the material referred to is or was part of the common general knowledge as at the filing date of the application.

SUMMARY OF THE INVENTION

In a first aspect, the present invention provides a core tray comprising a body including at least one channel arranged to hold at least one core sample, wherein the body includes at least one set of handles provided on both the major and minor axes, the handles of each of the set of handles being provided proximate each other and arranged to, in use, to allow a user to grip the core tray to assist in moving the core tray.

In one embodiment, the at least one set of handles include a plurality of ribs. Preferably, two sets of handles are provided at substantially opposite ends of the tray.

In one embodiment, a top lip of the tray and a bottom lip of the tray are of a complementary design such that two or more core trays may be stacked in a nesting fashion.

The handles may be integrally formed in the body of the tray.

In one embodiment, the handles do not protrude beyond the edge formed by the body of the core tray.

The at least one channel preferably includes at least one defined access recess arranged to, in use, allow a user to access the at least one core sample residing in the at least one channel.

The at least one channel may further include a plurality of ribs arranged to, in use, support the at least one core sample residing in the at least one channel.

In one embodiment, an underside portion of the tray is substantially flat to facilitate sliding of the tray across a surface.

In a second aspect, there is provided a core tray comprising a body including at least one channel arranged to hold at least one core sample, wherein the channel includes at least one defined access recess arranged to, in use, allow a user to access the at least one core sample residing in the at least one channel.

In a third aspect, there is provided a core tray comprising a body including at least one channel arranged to hold at least one core sample, wherein the channel includes a plurality of ribs arranged to, in use, support the at least one core sample residing in the at least one channel.

Embodiments of the core tray may be integrally formed, optionally, from a plastics material.

Embodiments of the core tray may be colour coded.

In a fourth aspect, there is provided a core tray comprising a body including at least one channel arranged to hold at least one core sample, wherein the body includes an underside portion that is substantially flat to facilitate sliding of the tray across a surface.

BRIEF DESCRIPTION OF THE DRAWINGS

Notwithstanding any other forms which may fall within the scope of the present invention, a preferred embodiment will now be described, by way of example only, with reference to the accompanying drawings in which:

FIGS. 9a to 9d are diagrams illustrating a top view of further embodiments of a core tray;

DESCRIPTION OF EMBODIMENTS

Figure 1:
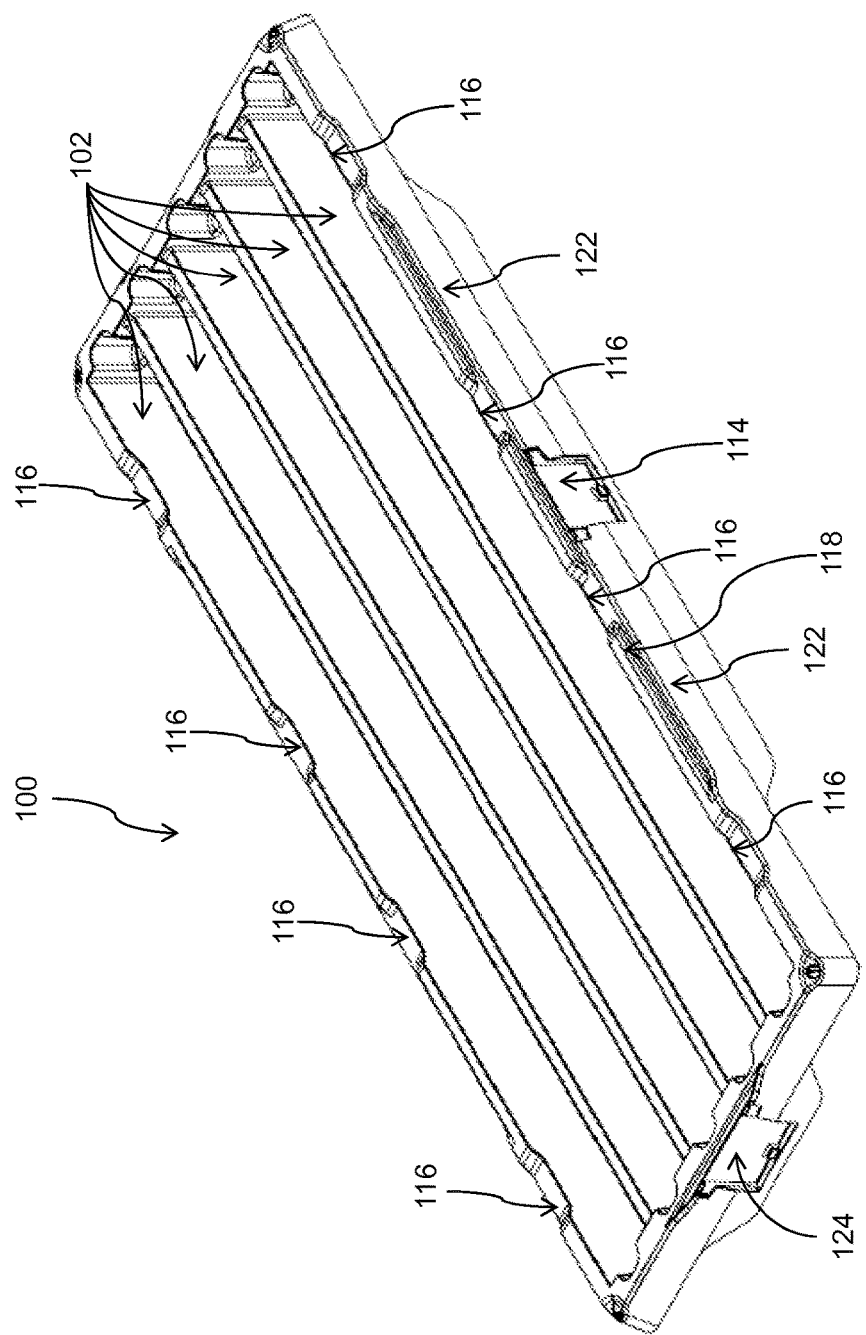
FIG. 1 is a diagram illustrating a top isometric view of a first embodiment of a core tray.
Figure 2:
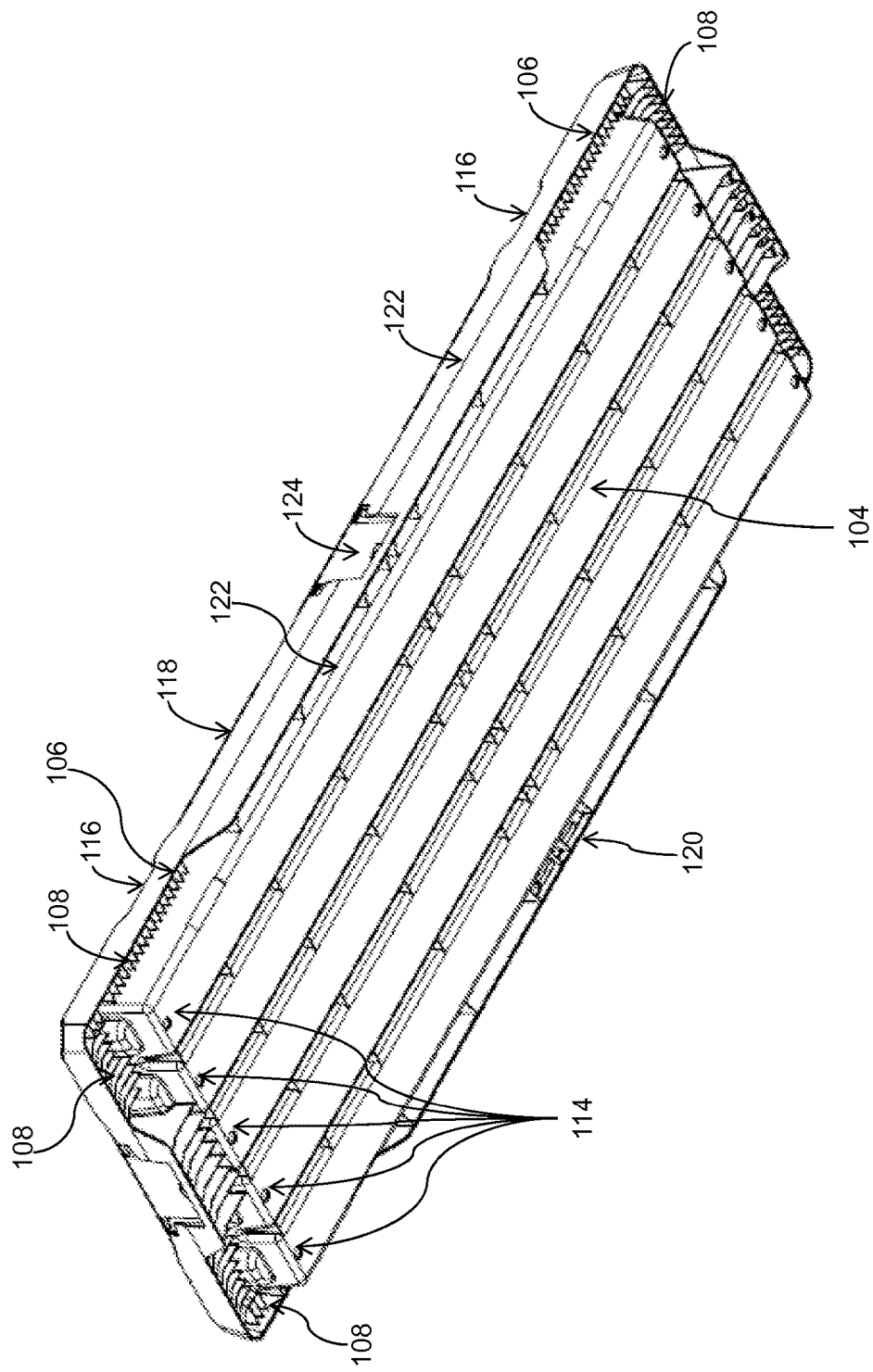
FIG. 2 is a diagram illustrating a bottom isometric view of a first embodiment of a core tray.
Figure 3:
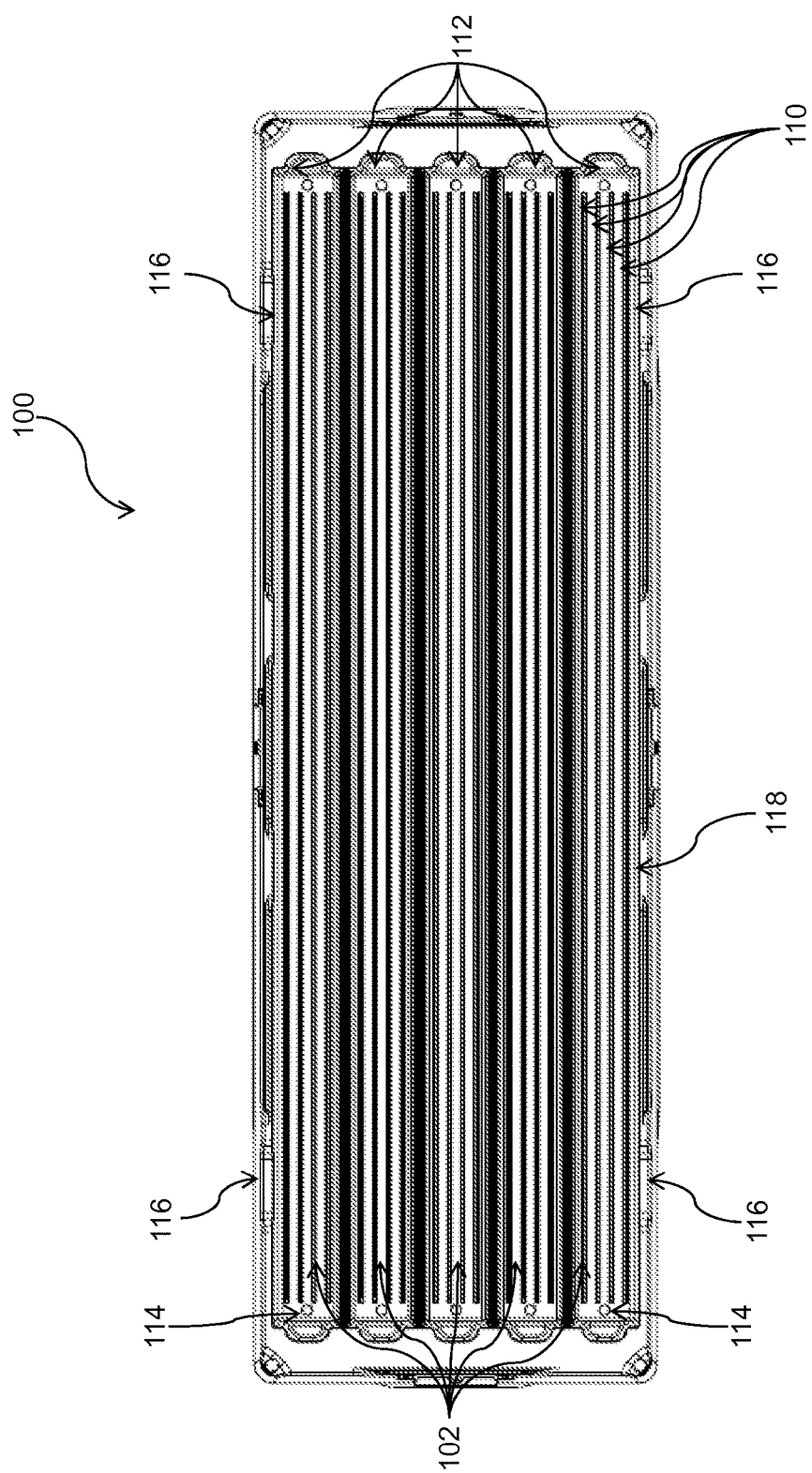
FIG. 3 is a diagram illustrating a top view of a first embodiment of a core tray.
Figure 4:
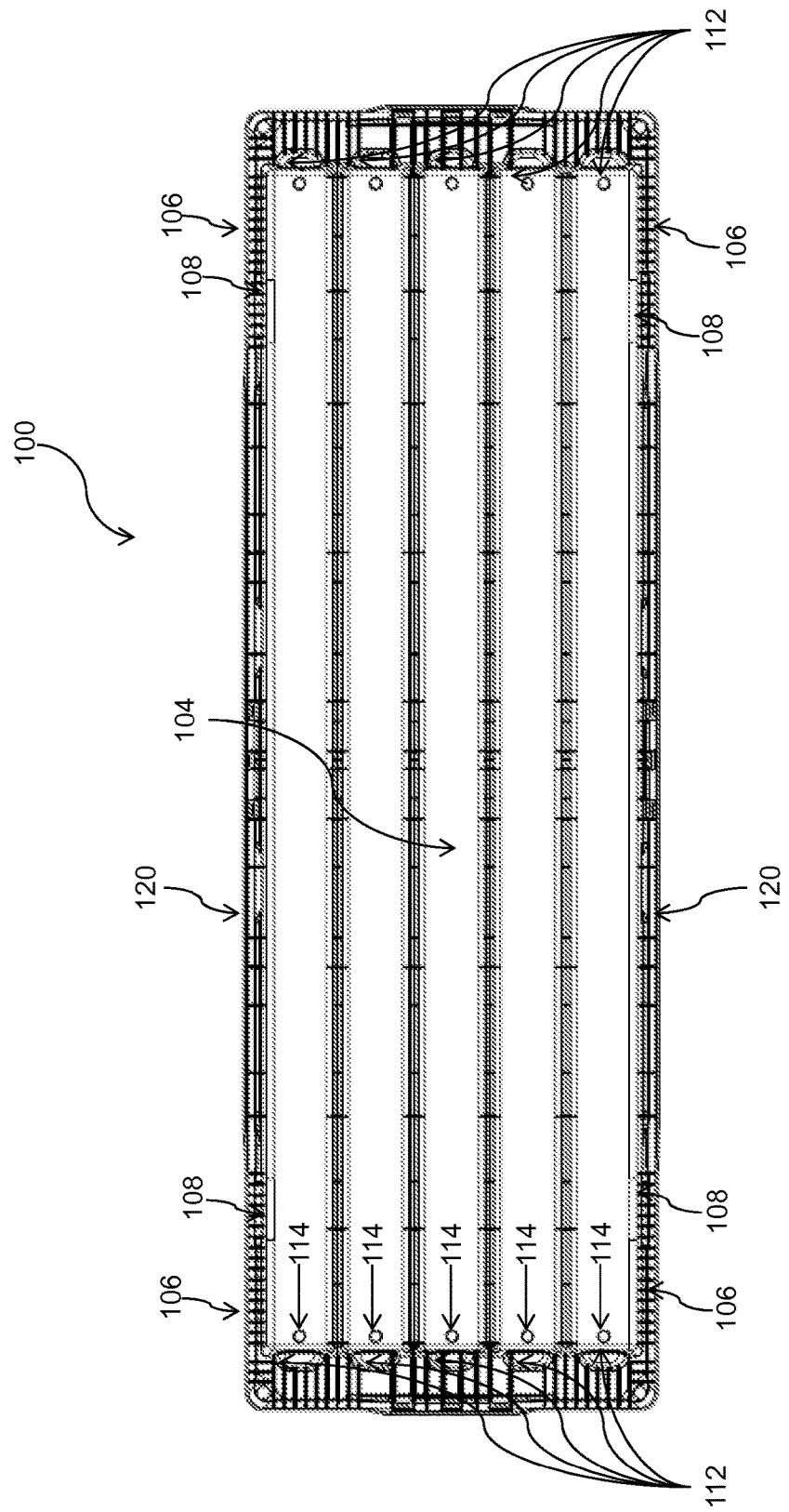
FIG. 4 is a diagram illustrating a bottom view of a first embodiment of a core tray.
Figure 5:
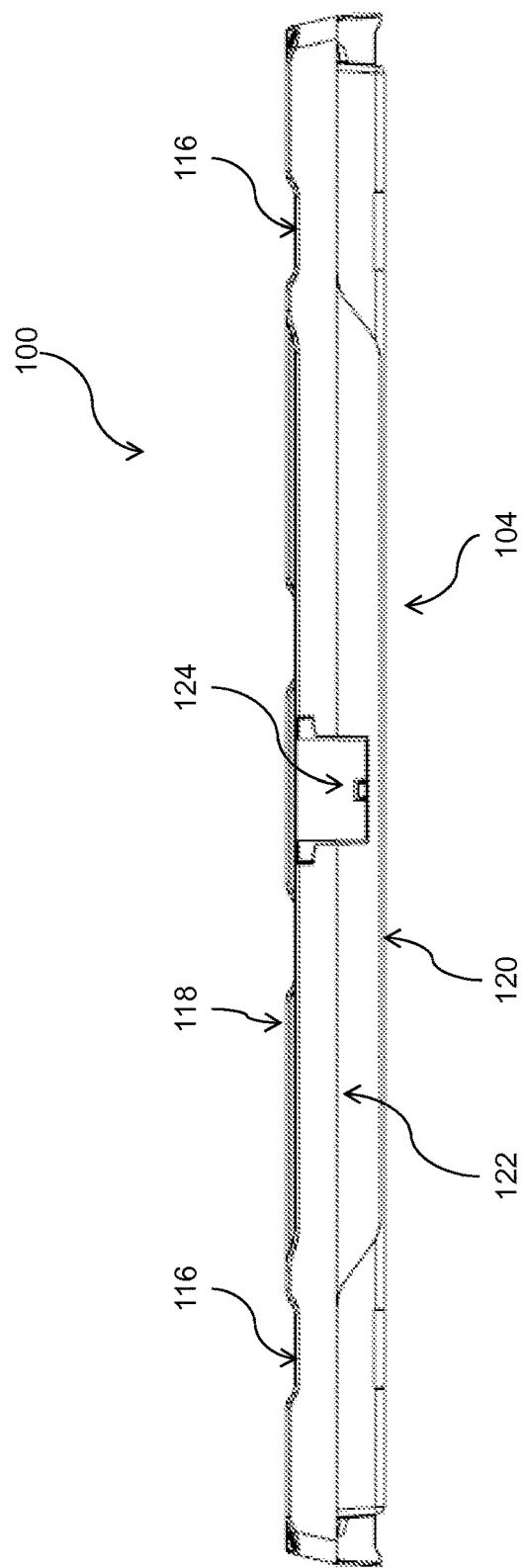
FIG. 5 is a diagram illustrating a side view (along a first side) of a first embodiment of a core tray.
Figure 6:
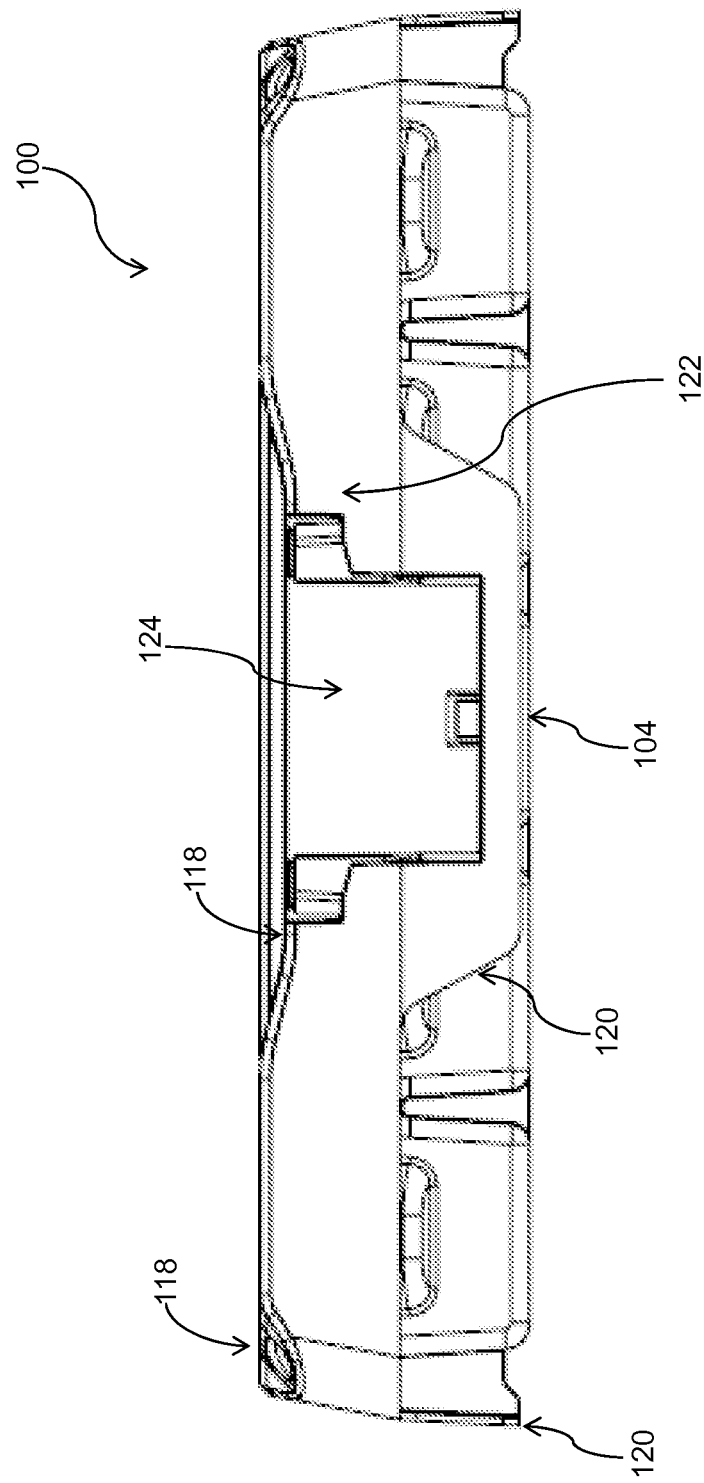
FIG. 6 is a diagram illustrating a side view (along a second side) of a first embodiment of a core tray.
Figure 7A:
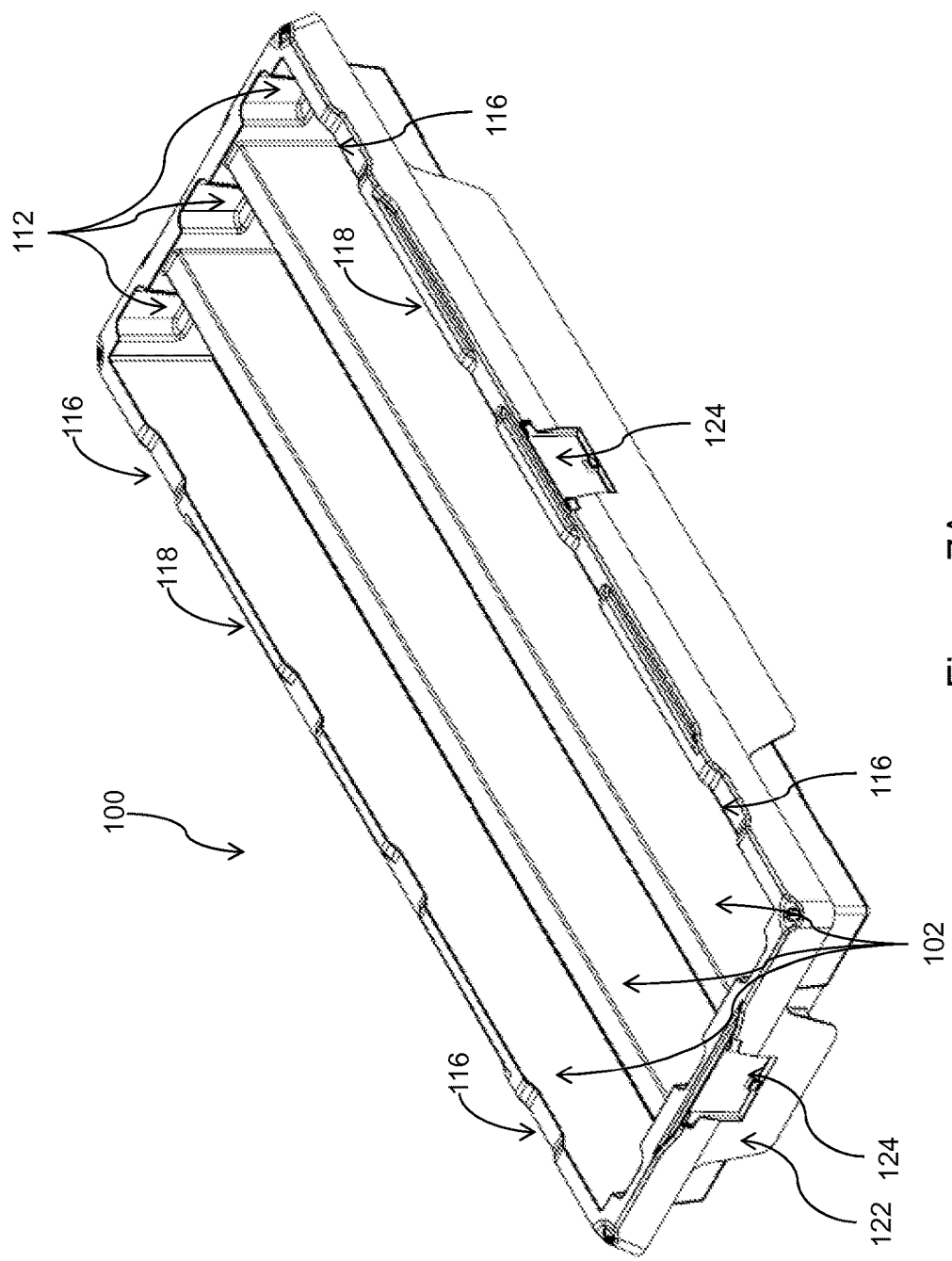
FIGS. 7a to 7d are diagrams illustrating a top isometric view of respective further embodiments of a core tray.
Figure 7B:
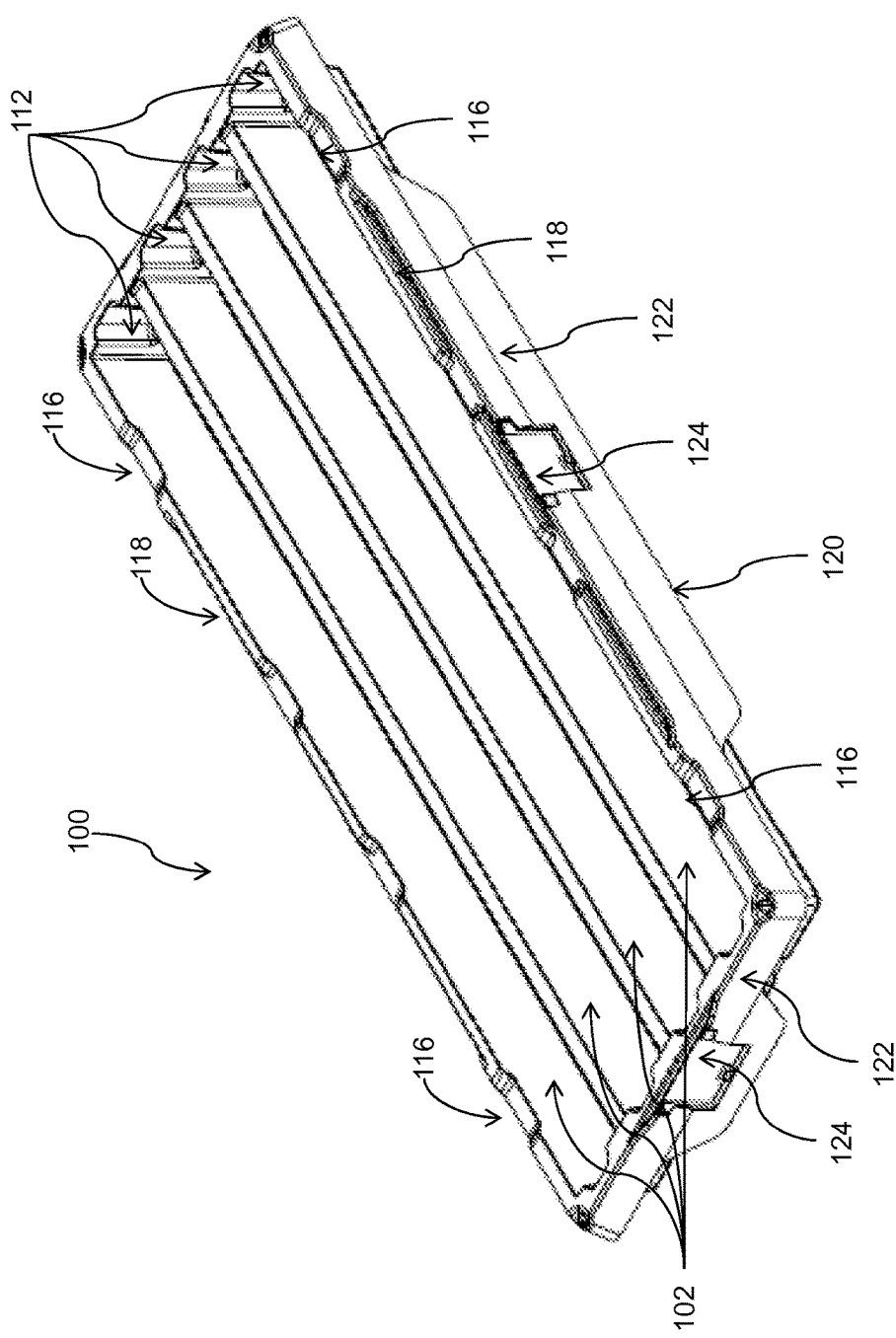
Figure 7C:
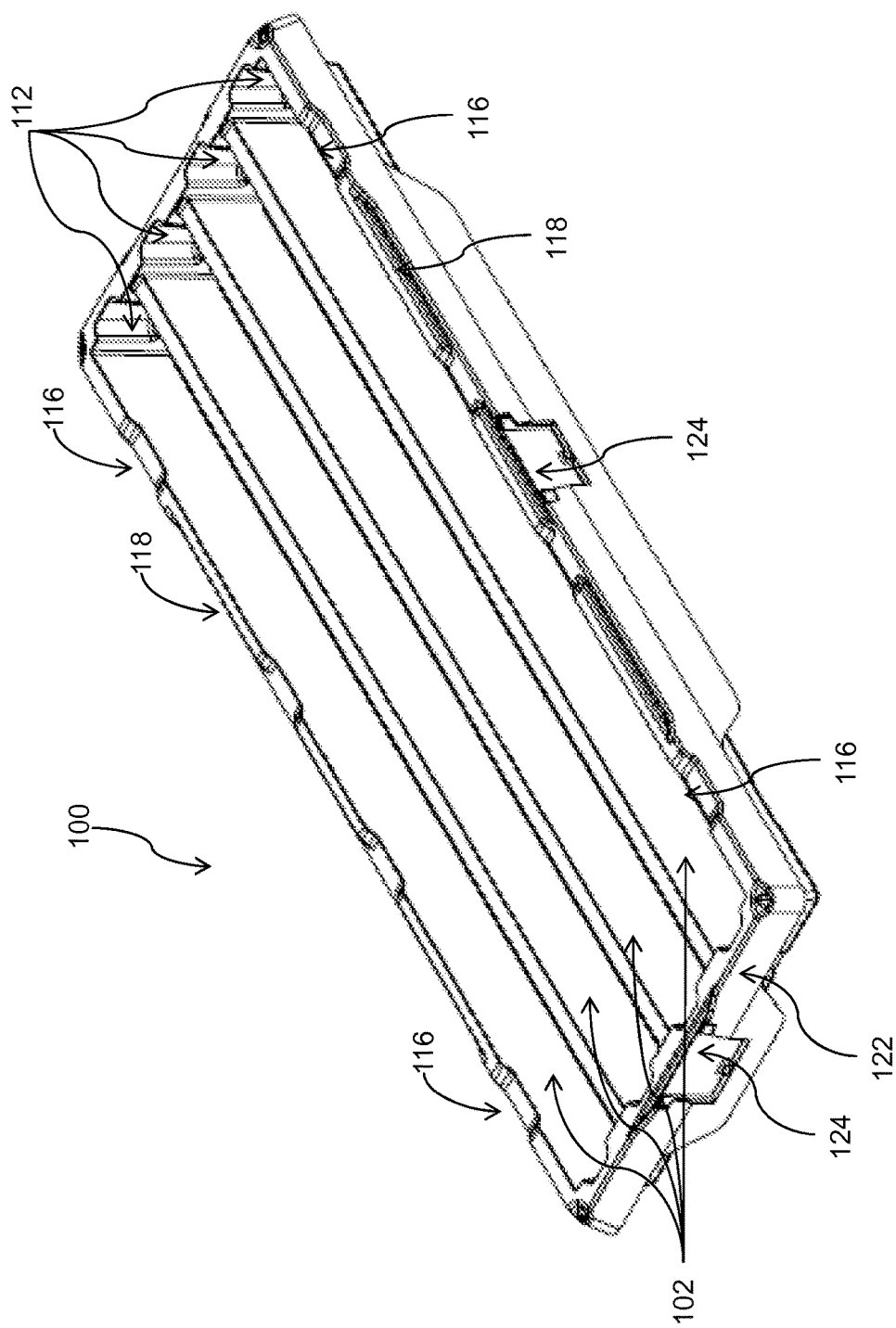
Figure 7D:
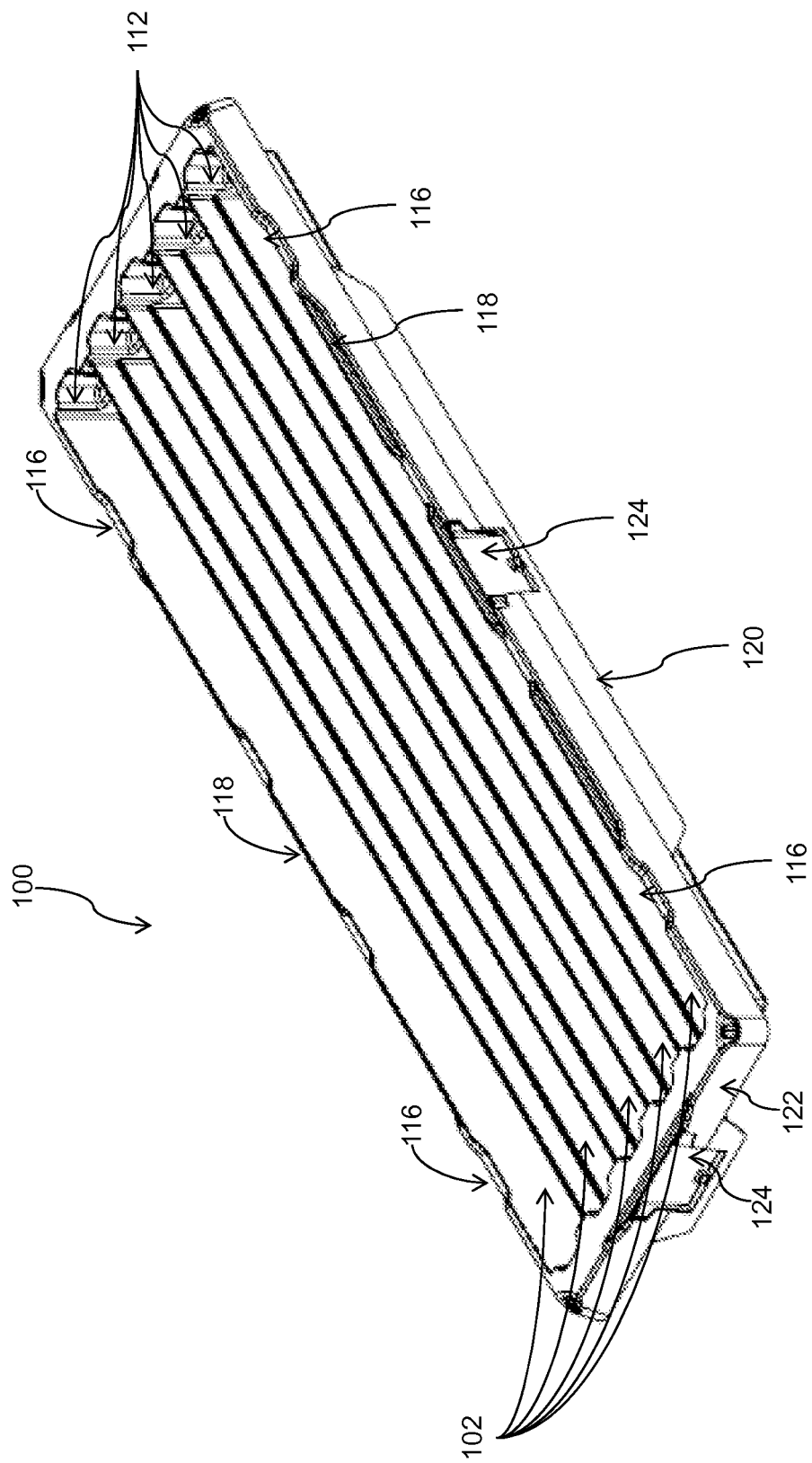
Figure 8A:
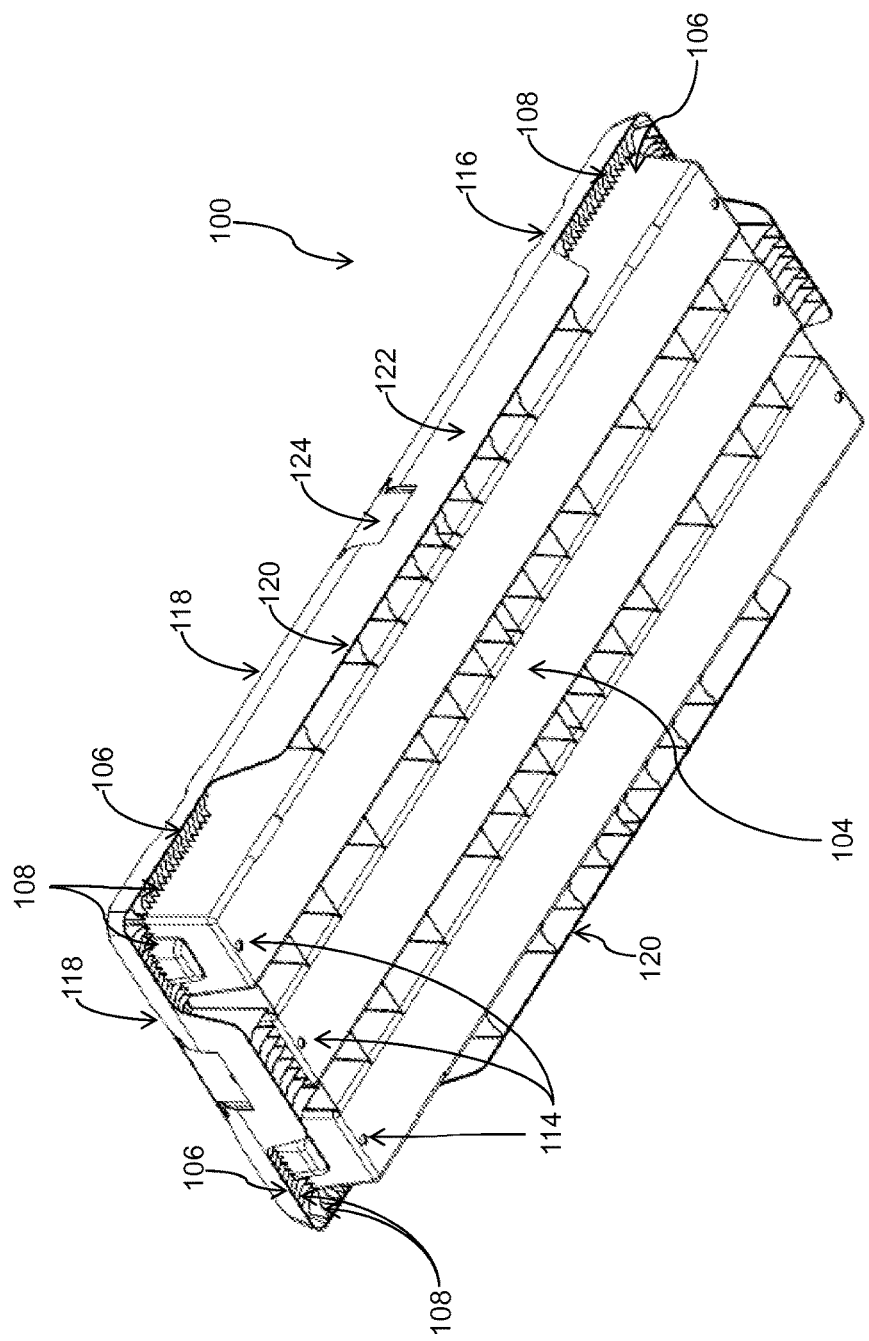
FIGS. 8a to 8d are diagrams illustrating a bottom isometric view of further embodiments of a core tray.
Figure 8B:
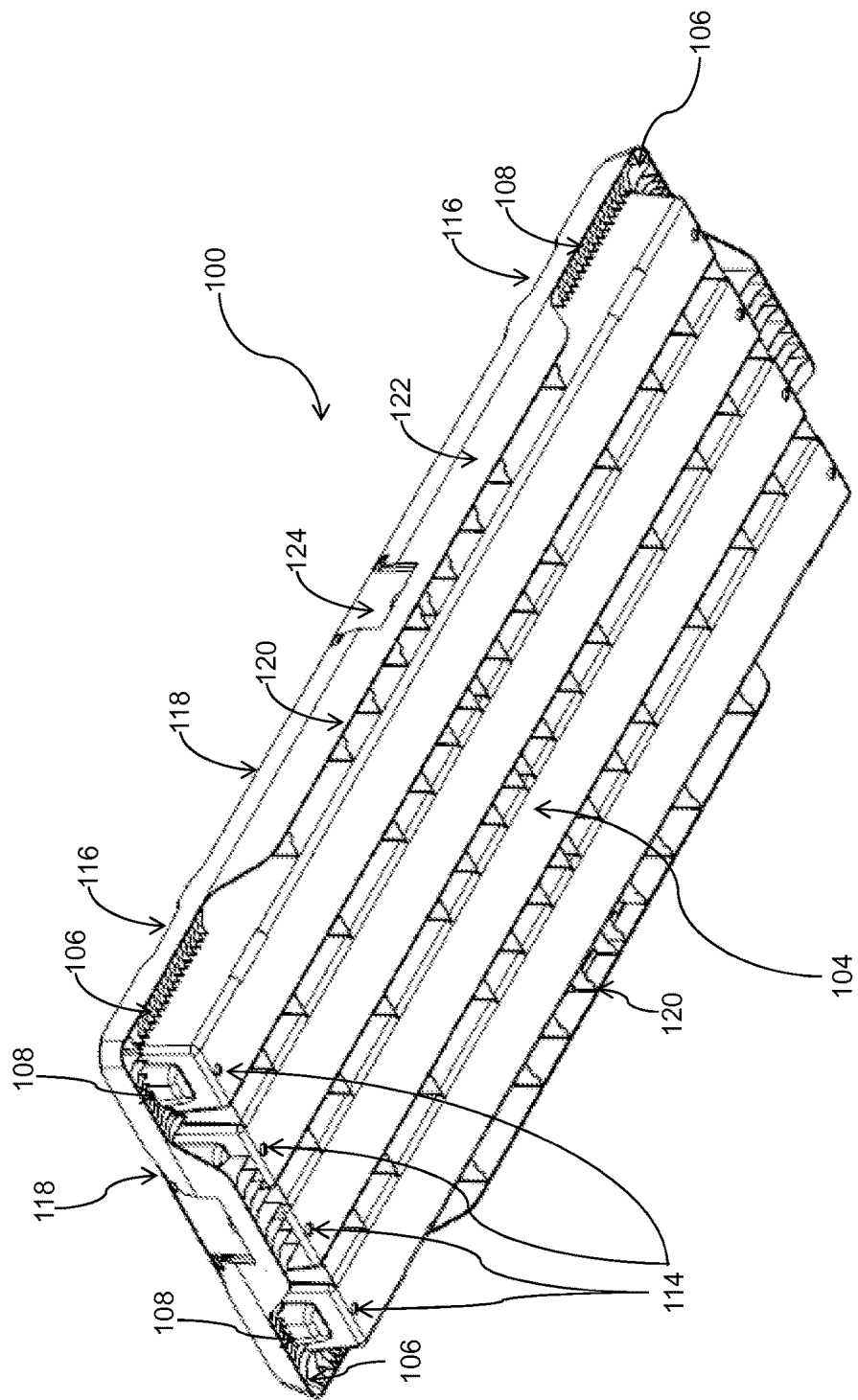
Figure 8C:
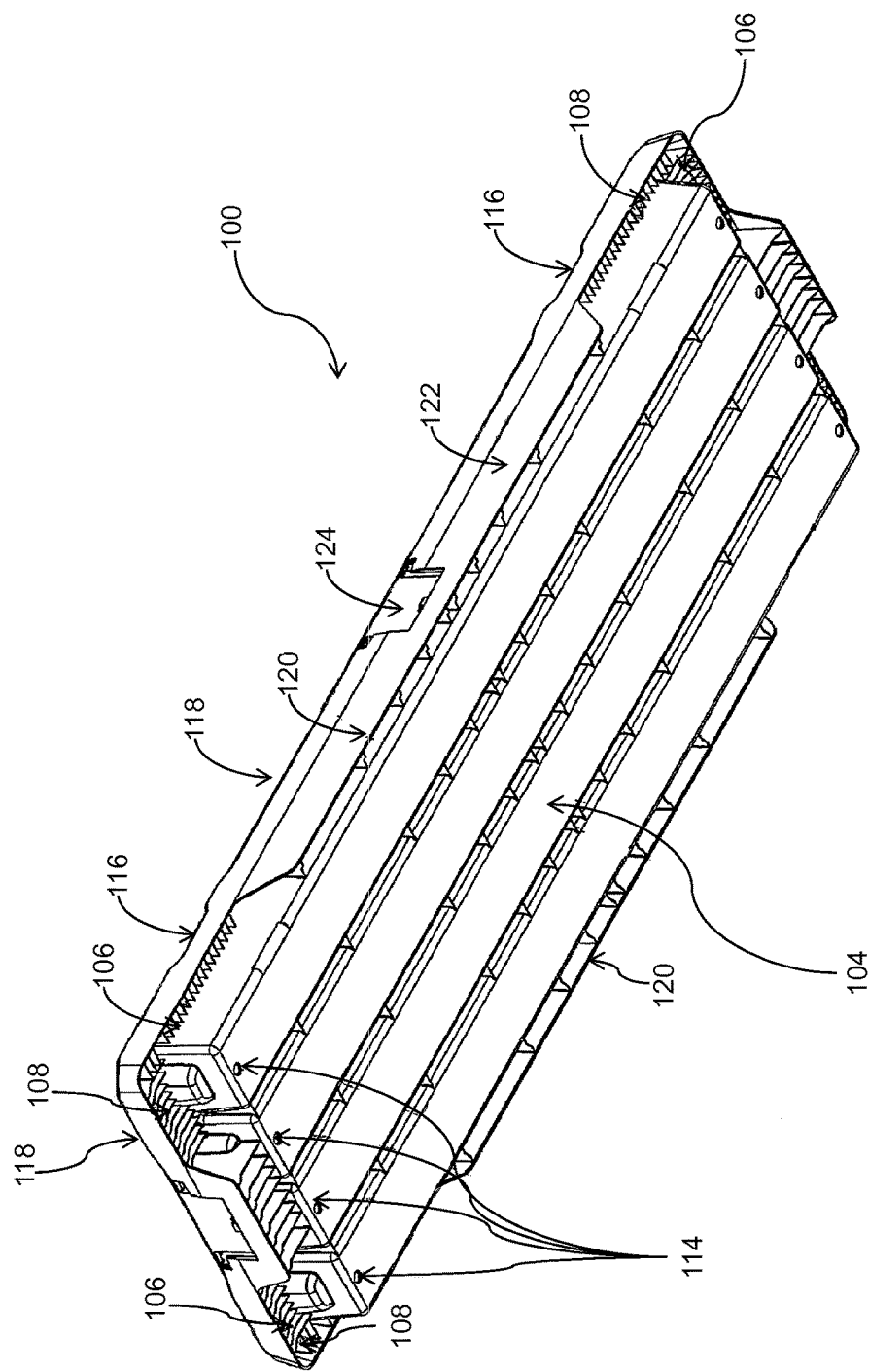
Figure 8D:
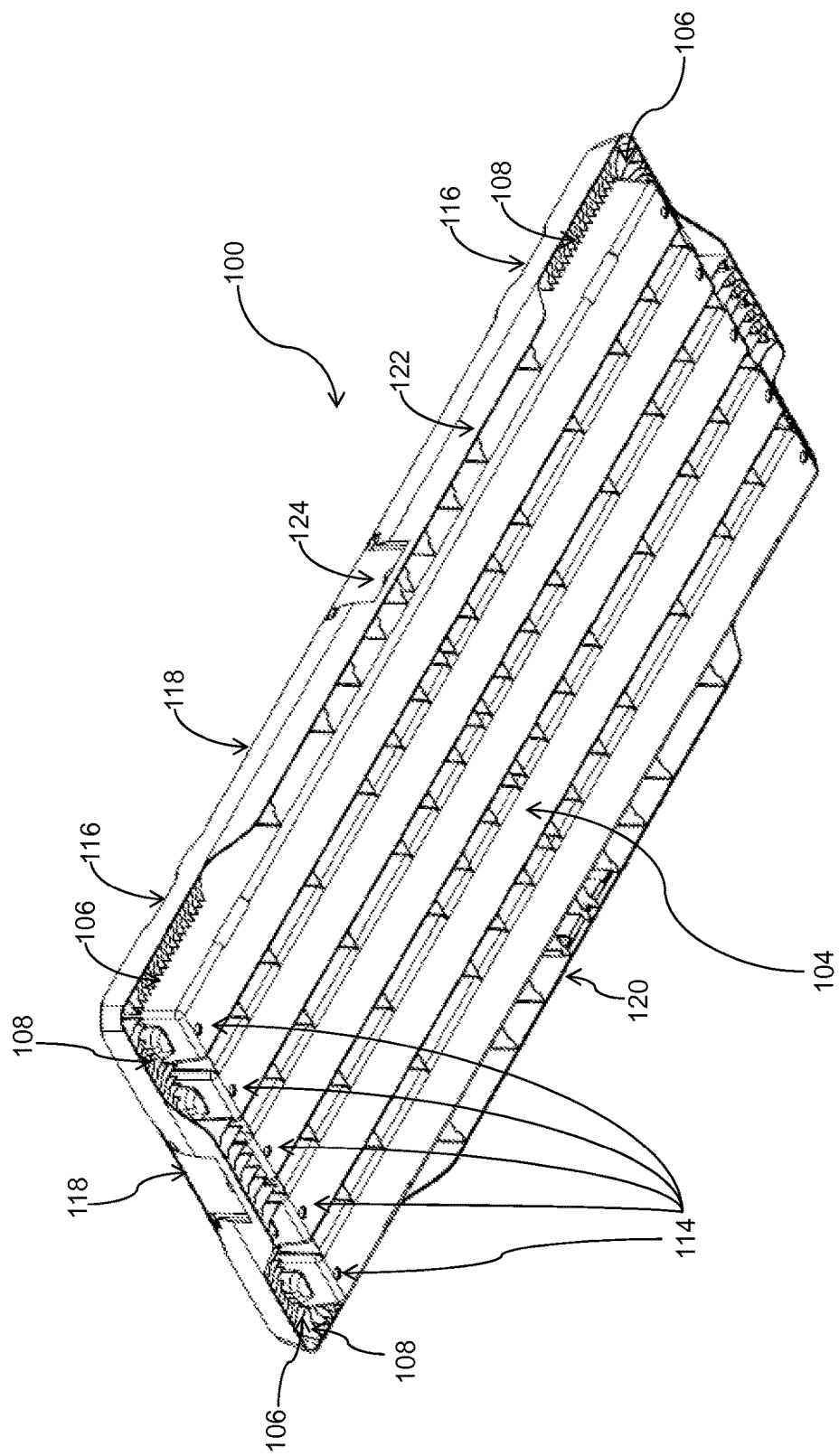
Figure 9A:
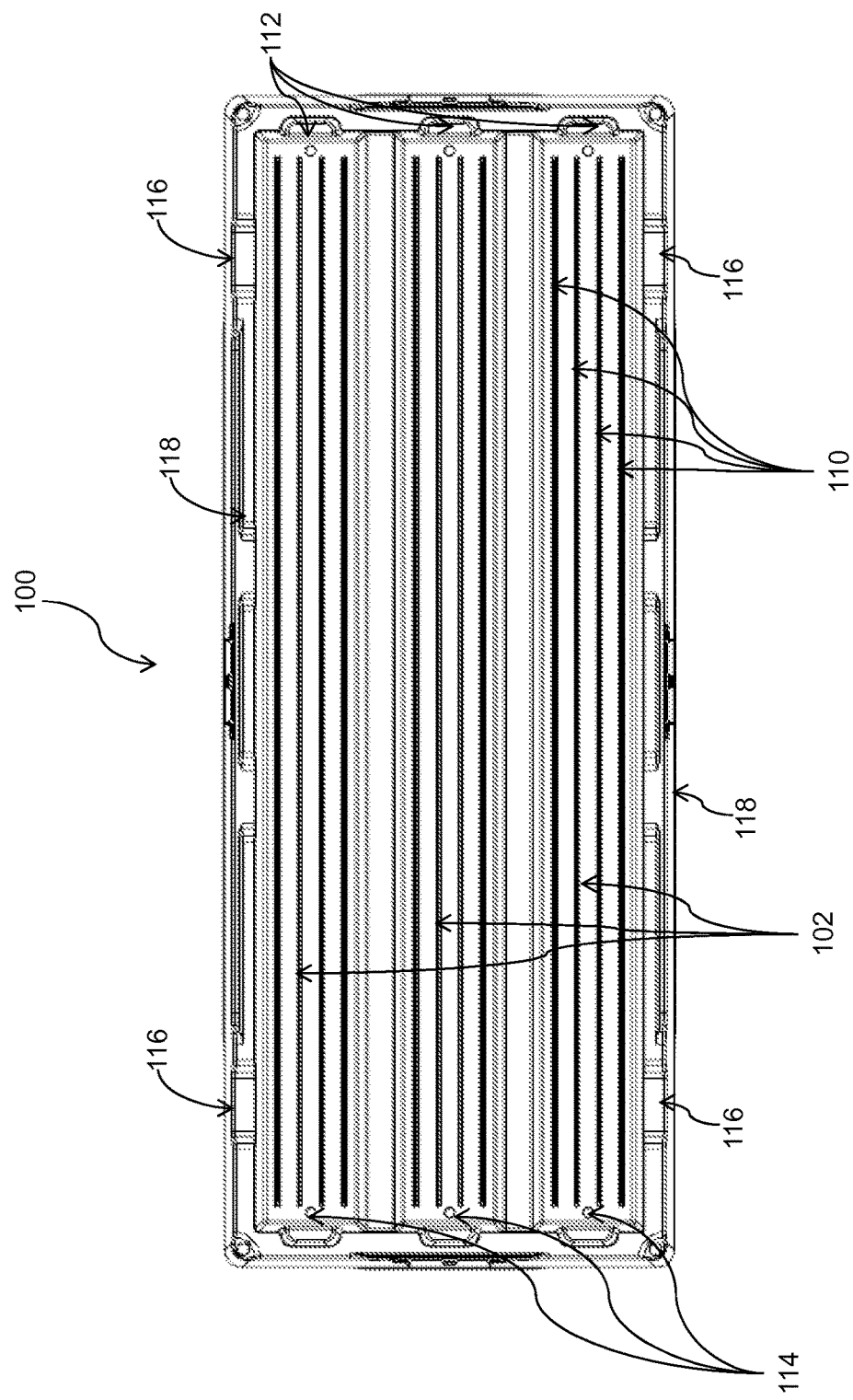
Figure 9B:
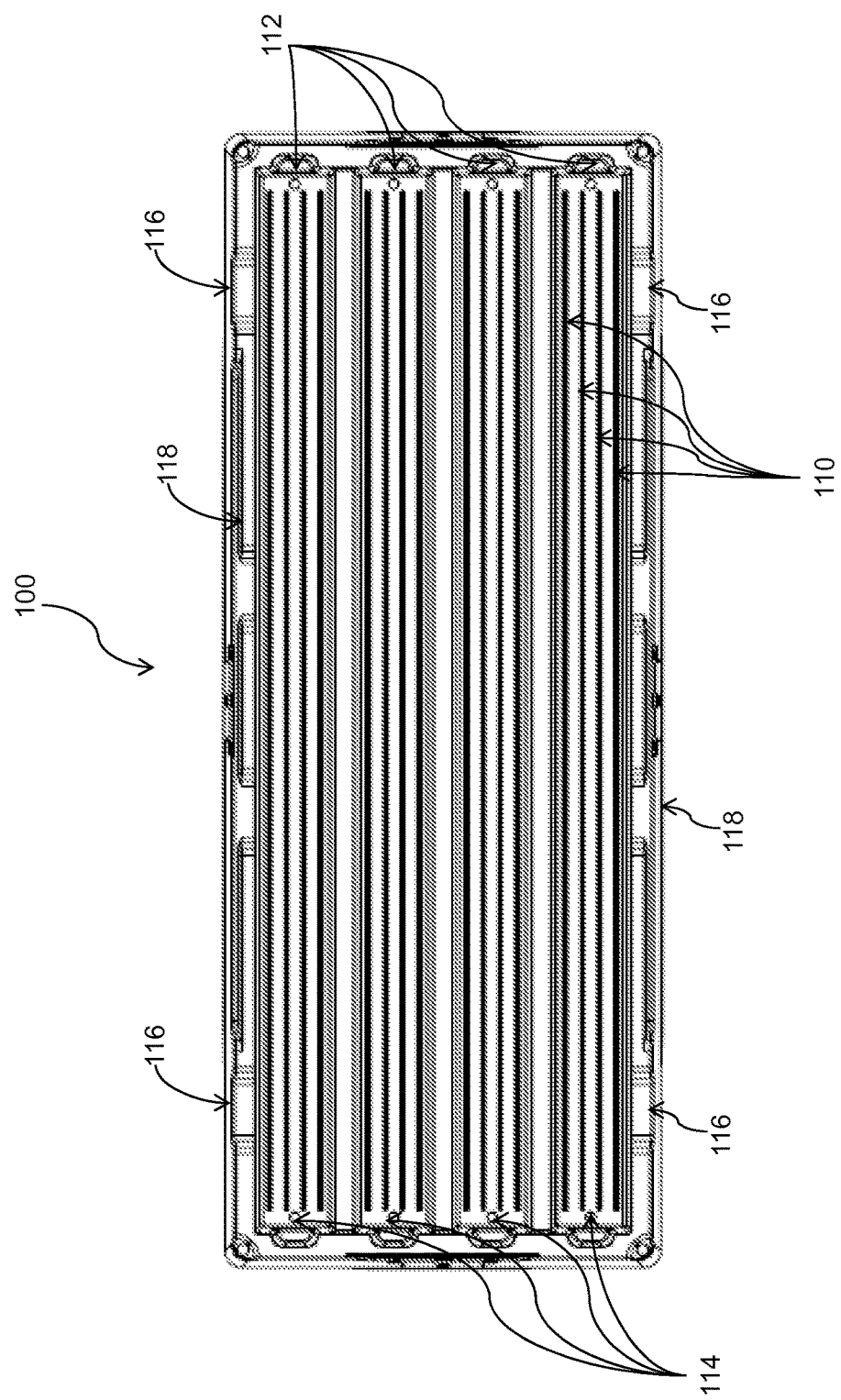
Figure 9C:
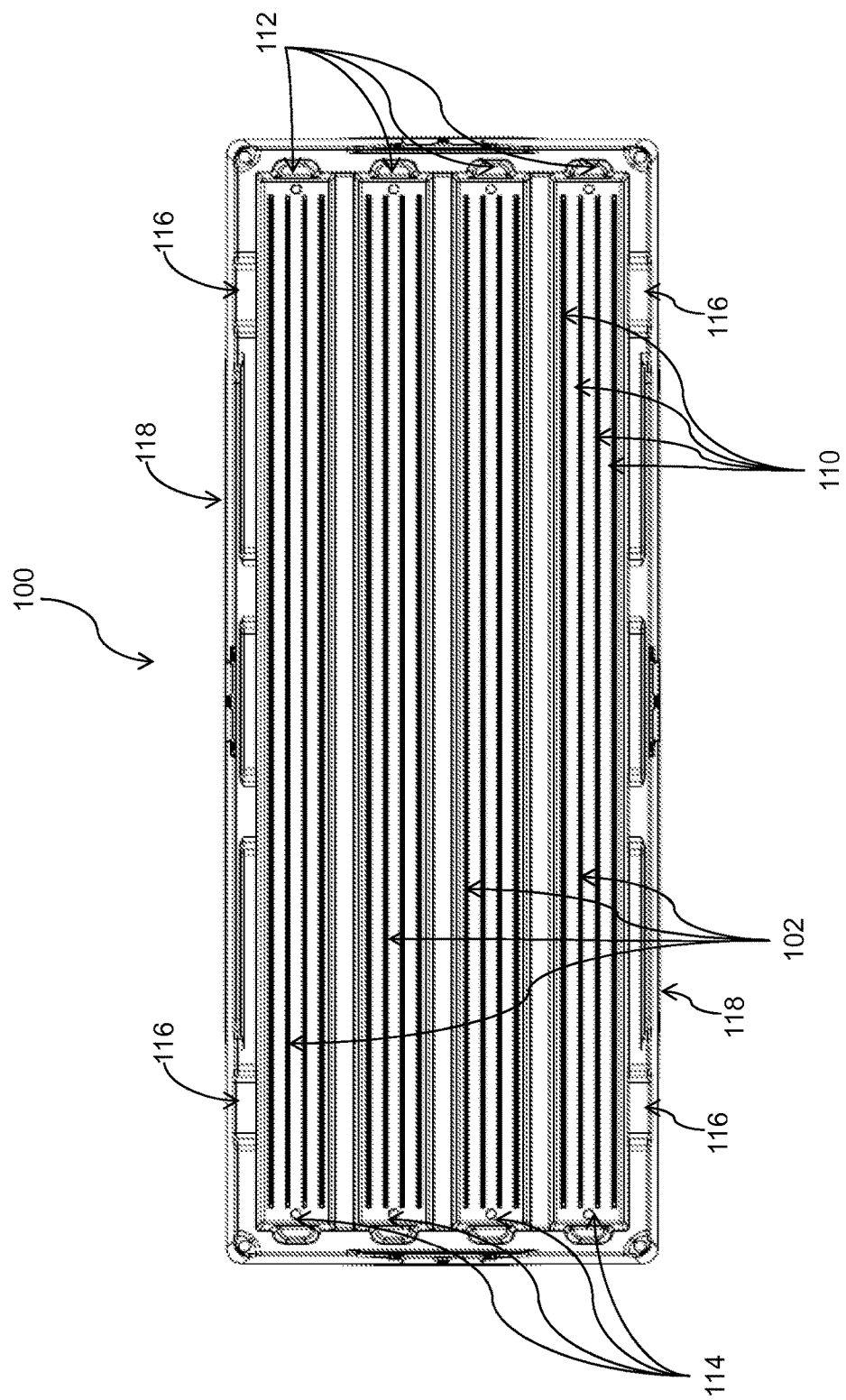
Figure 10A:
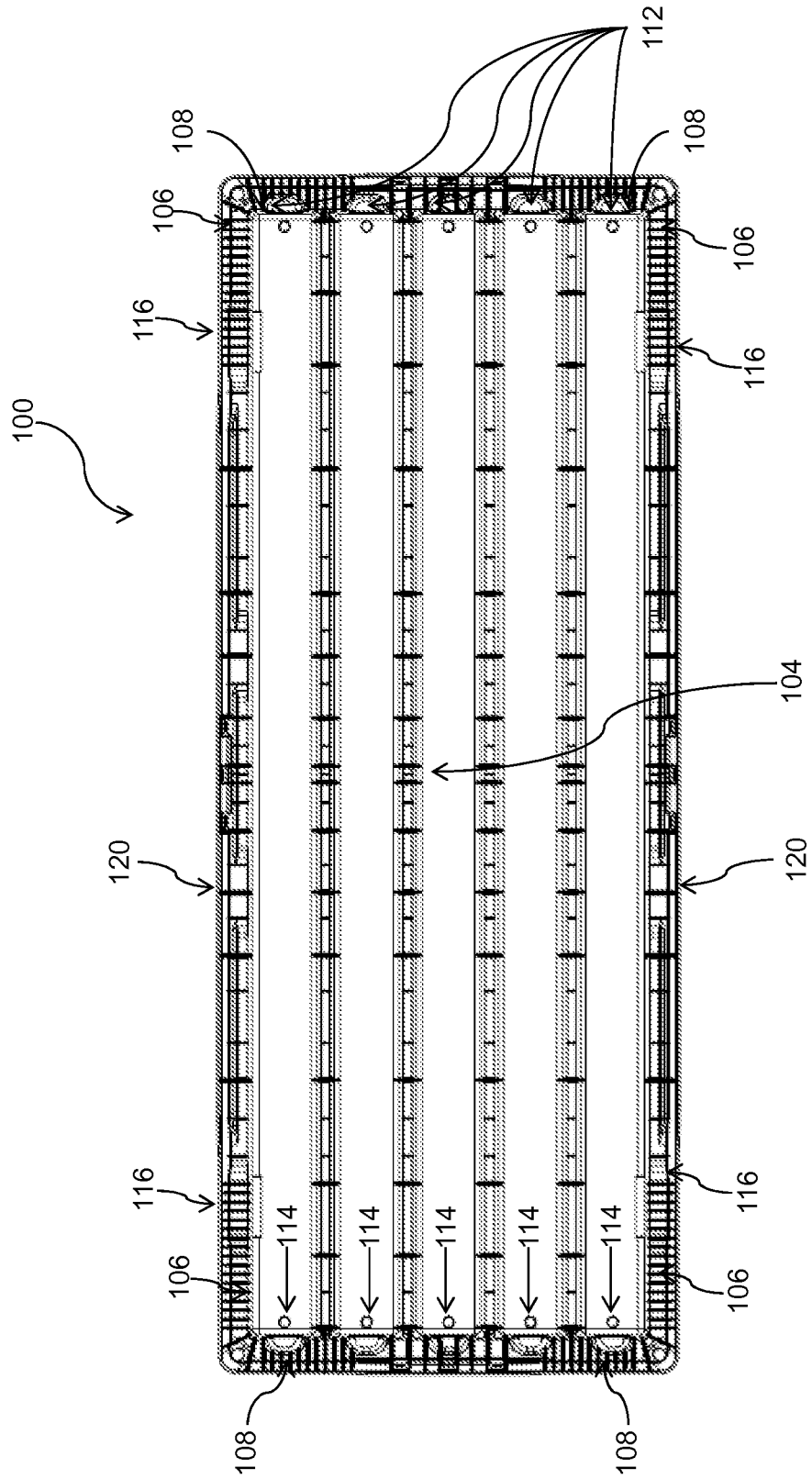
FIGS. 10a to 10d are diagrams illustrating a bottom view of further embodiments of a core tray.
Figure 10B:
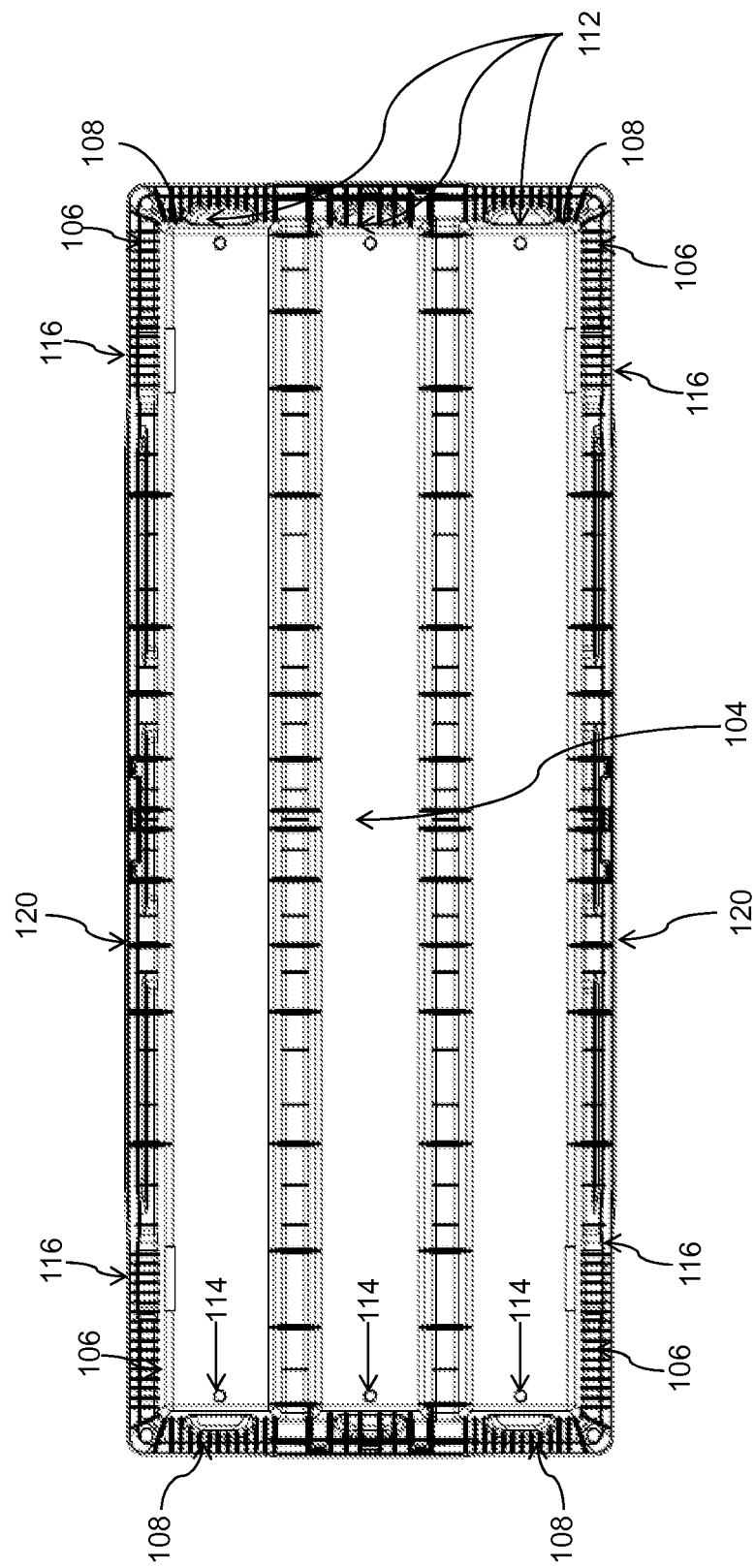
Figure 10C:
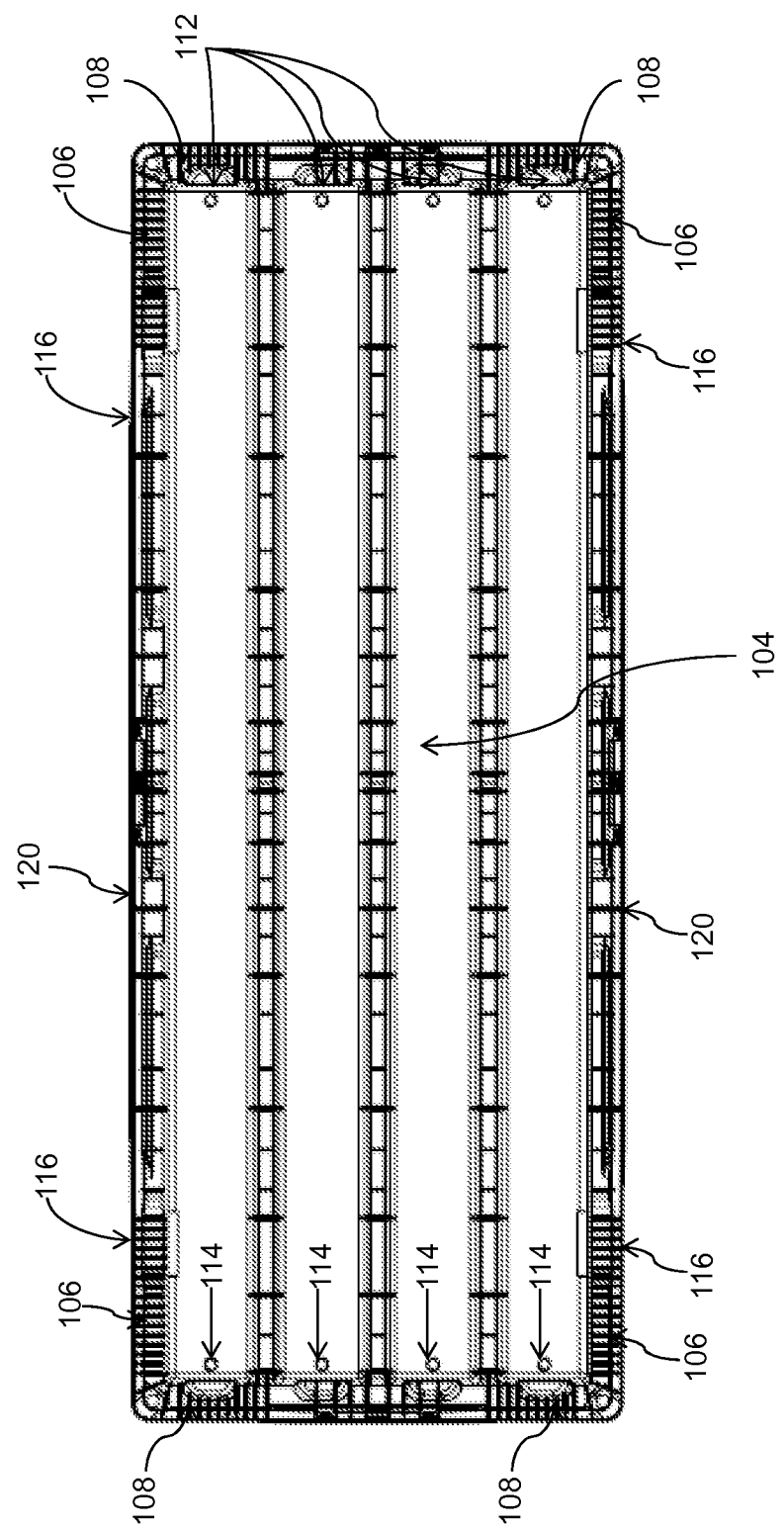
Figure 10D:
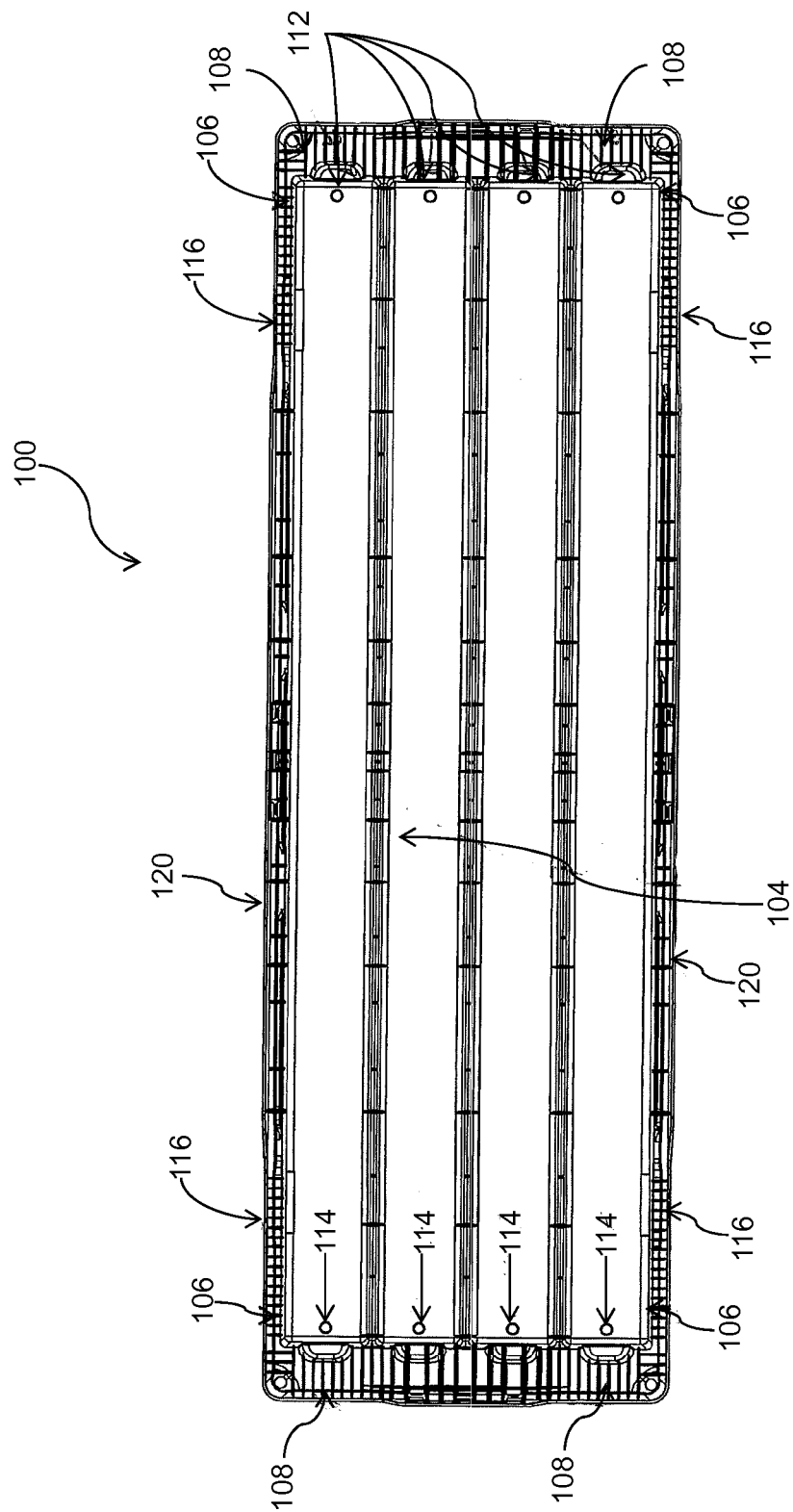
Figure 11A:
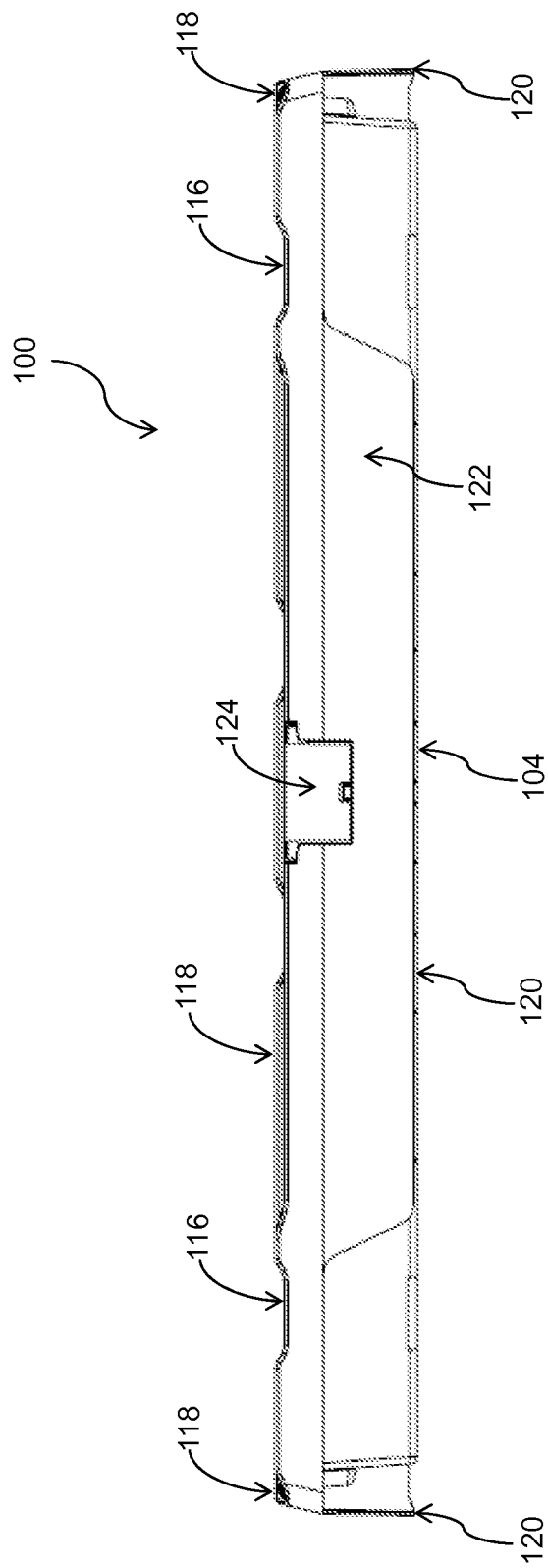
FIGS. 11a to 11d are diagrams illustrating a side view (along a first side) of further embodiments of a core tray.
Figure 11B:
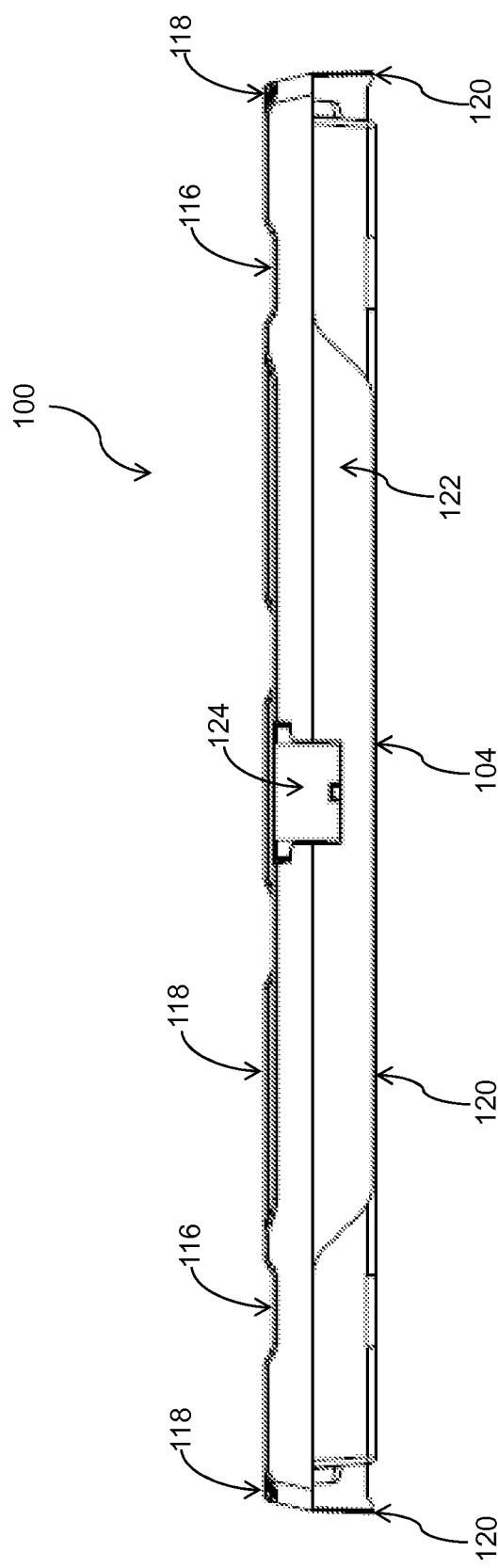
Figure 11C:
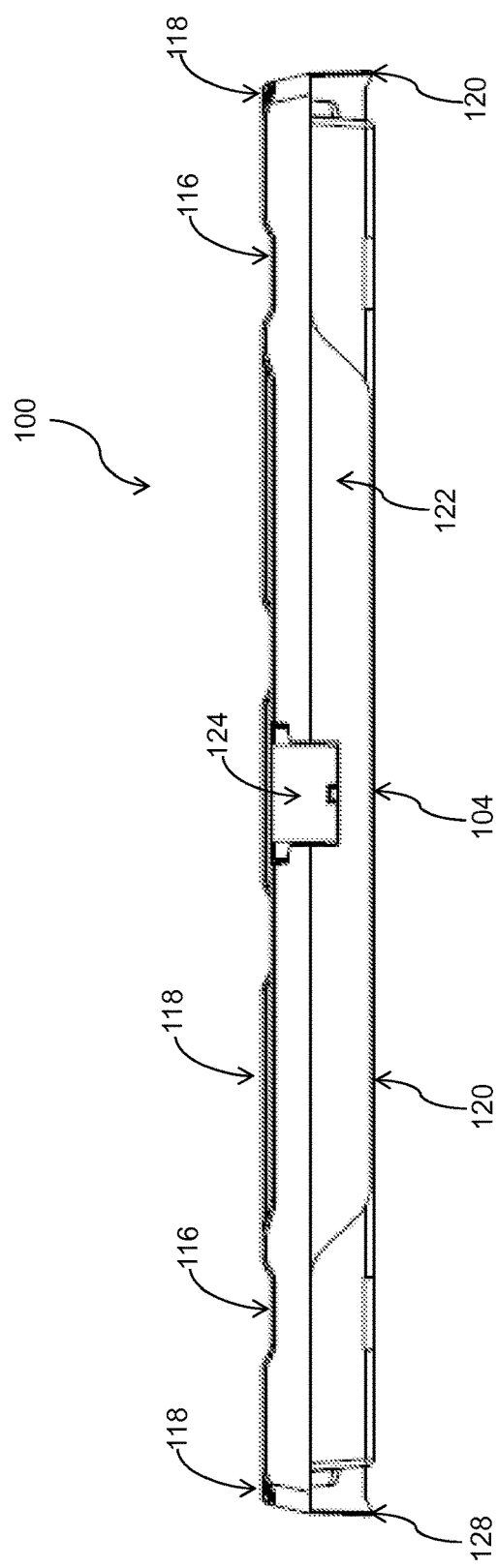
Figure 11D:
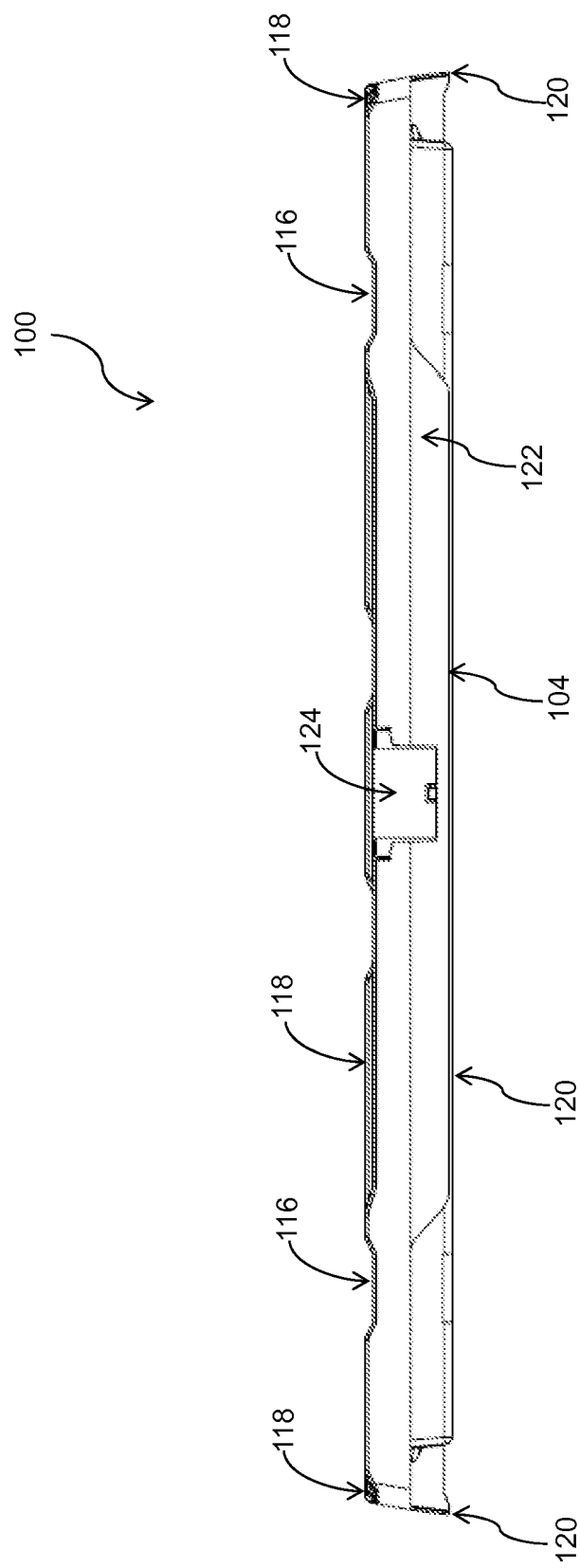
Figure 12A:
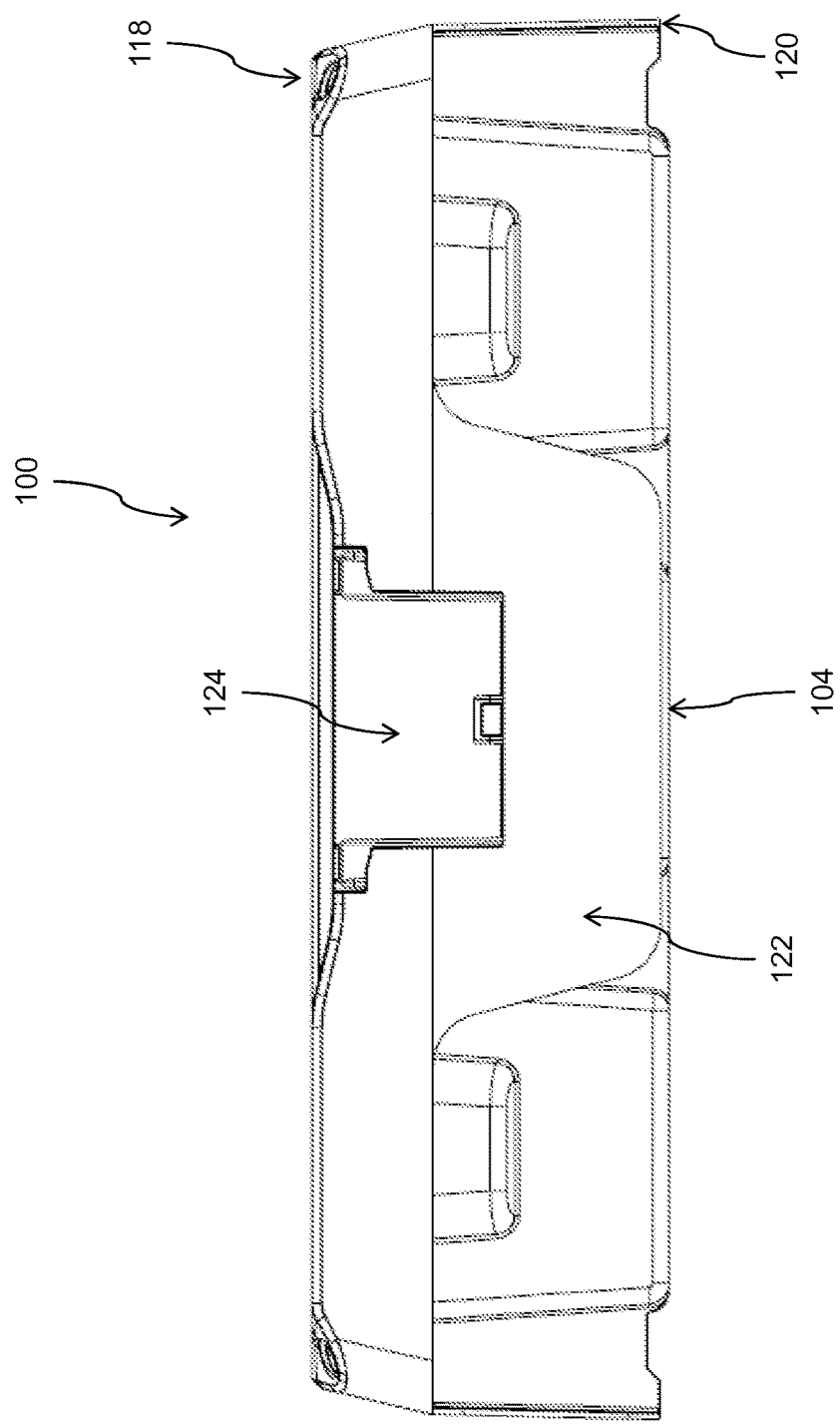
FIGS. 12a to 12d are diagrams illustrating a side view (along a second side) of further embodiments of a core tray.
Figure 12B:
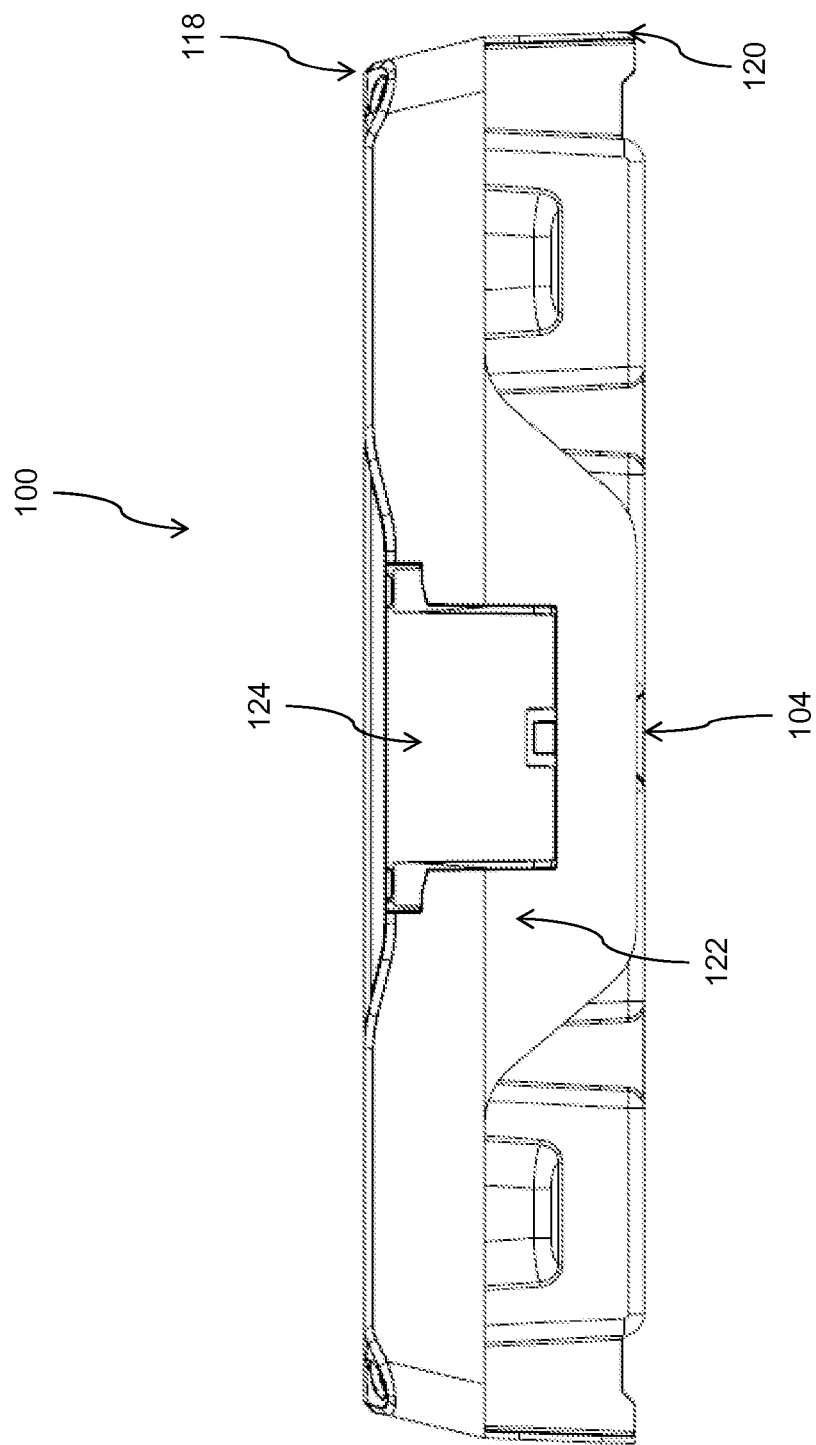
Figure 12C:
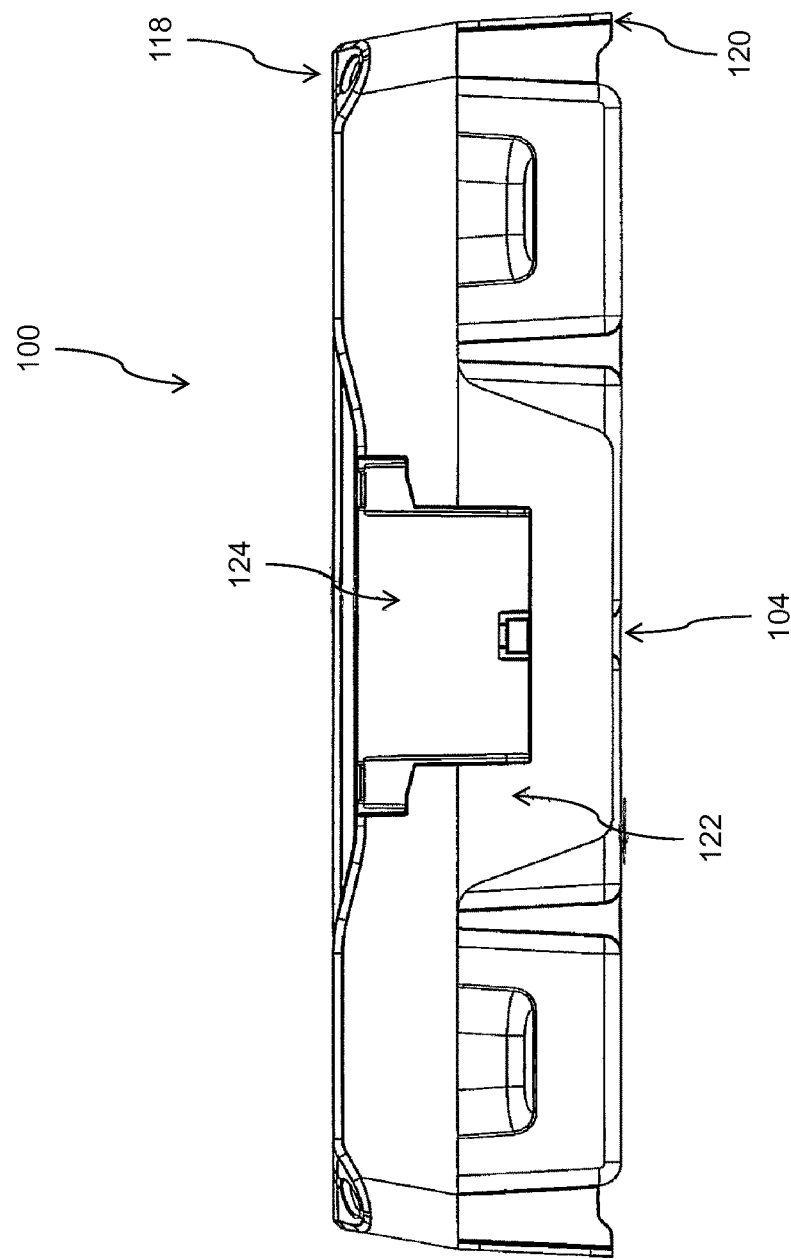
Figure 12D:
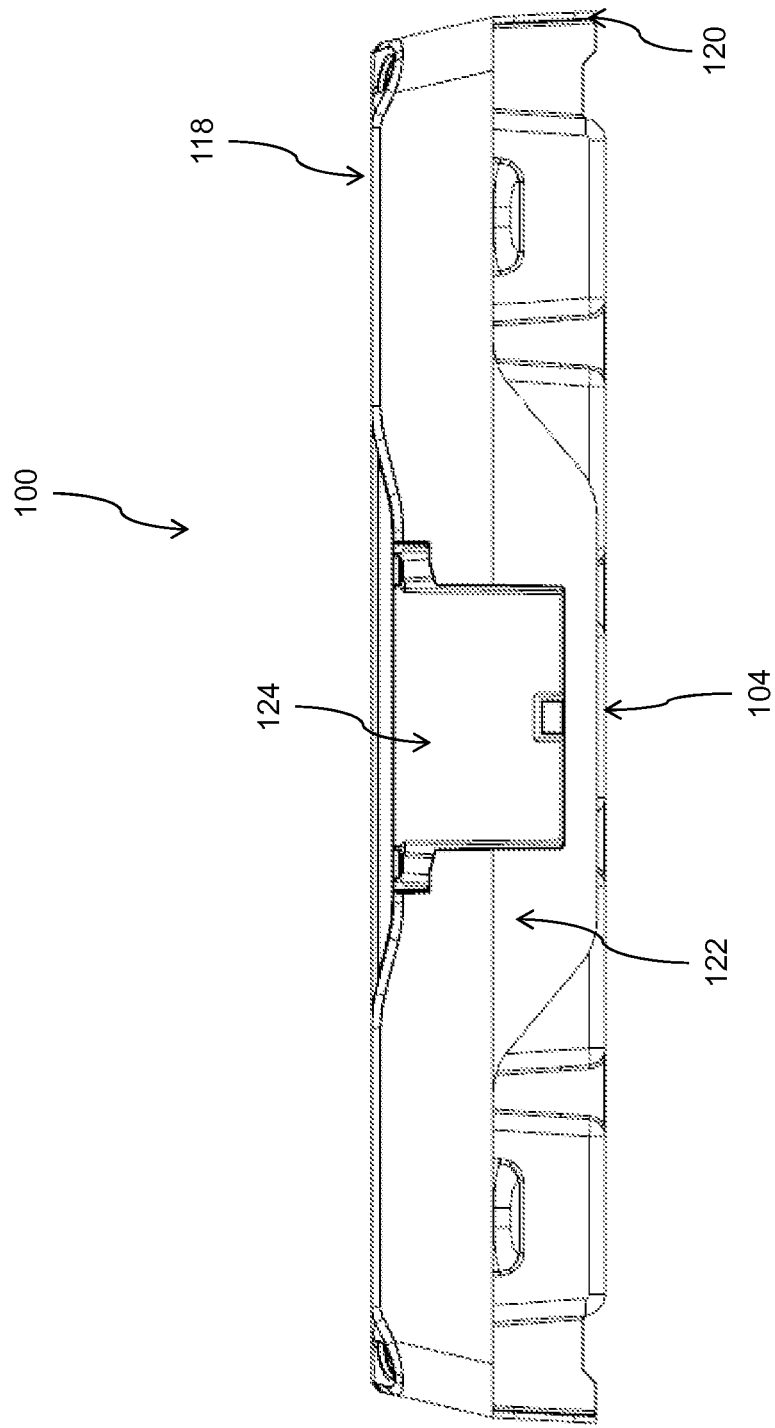
Figure 13:
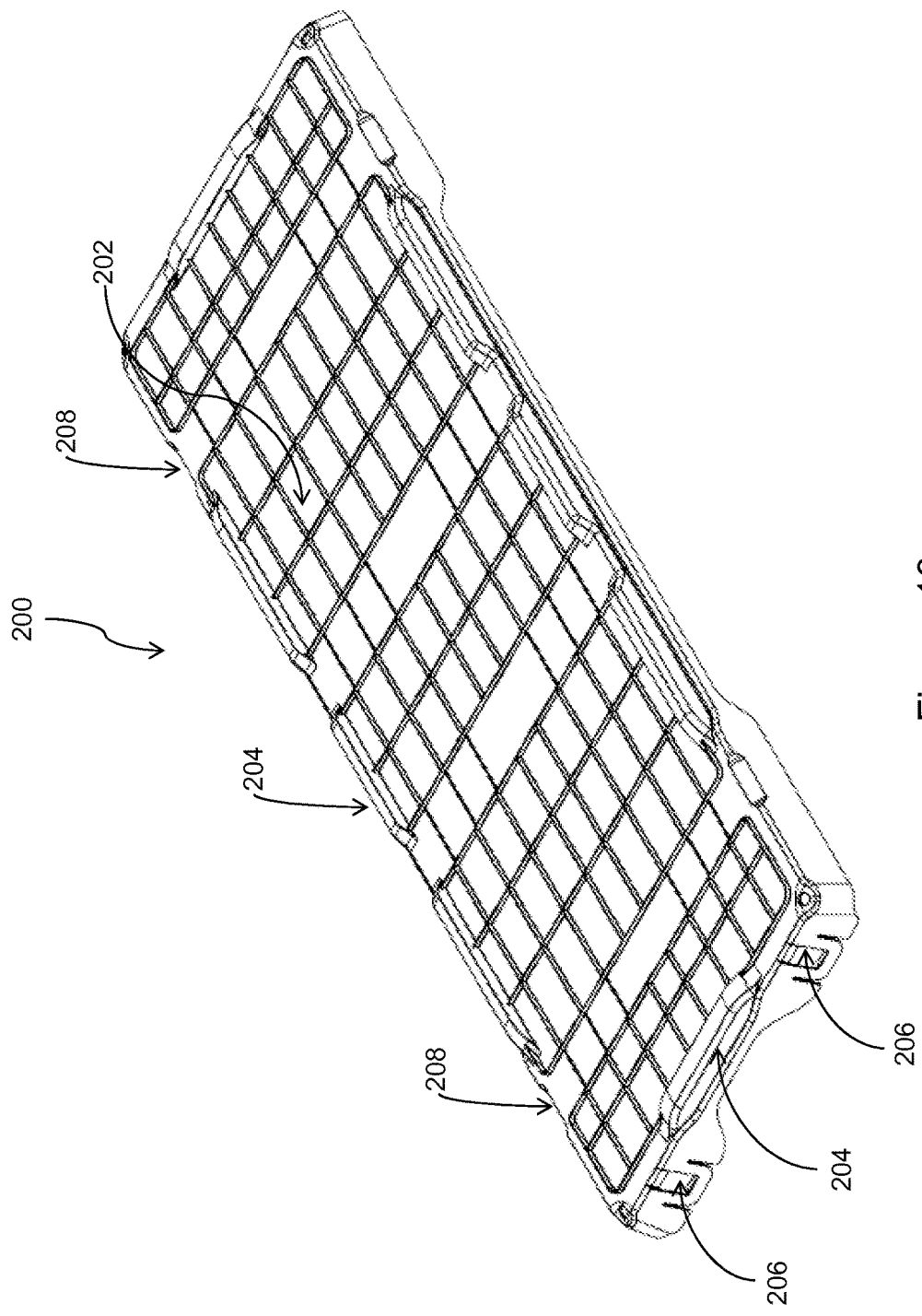
FIG. 13 is a diagram illustrating a top isometric view of a lid.
Figure 14:
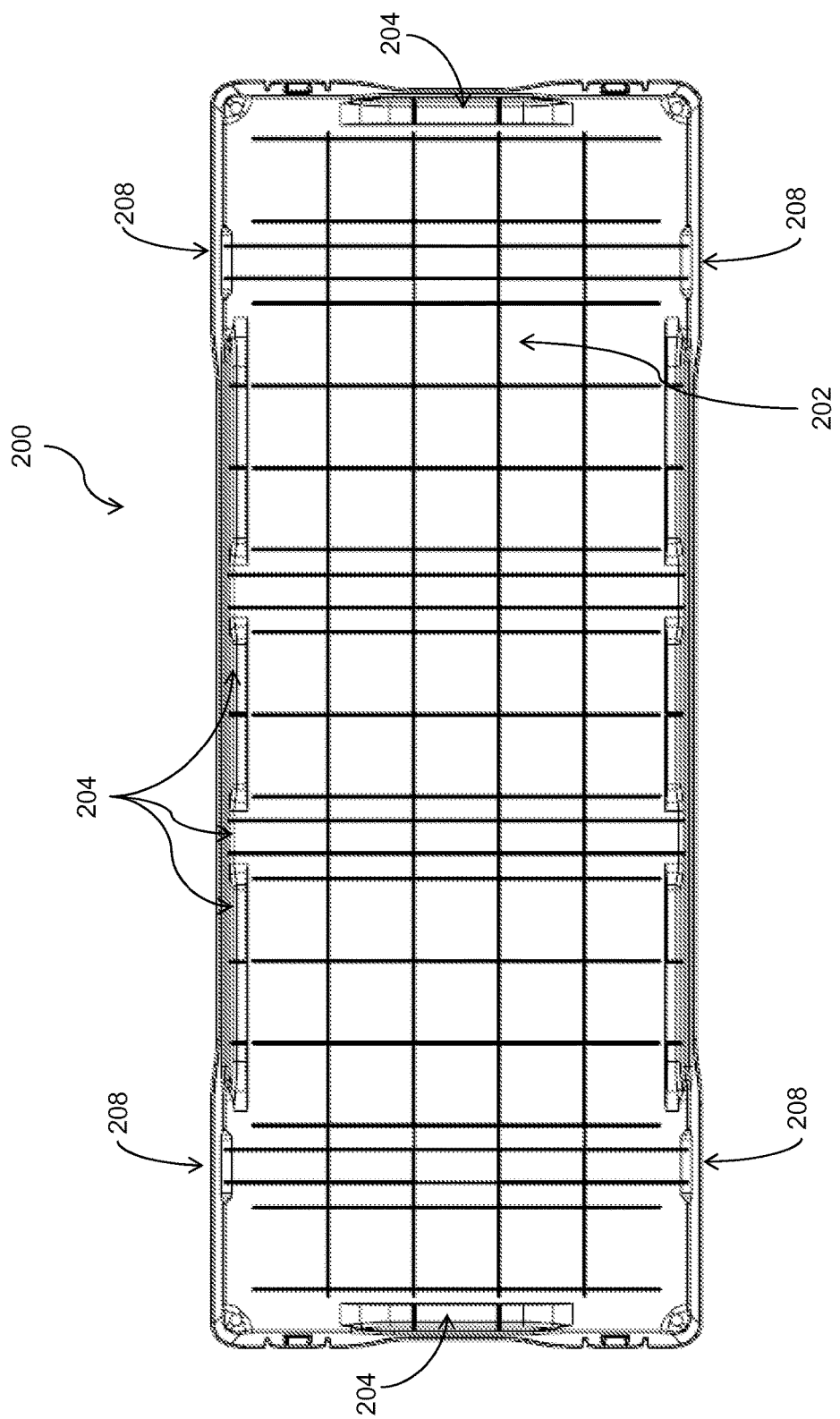
FIG. 14 is a diagram illustrating a top view of a first embodiment of a lid.
Figure 15:
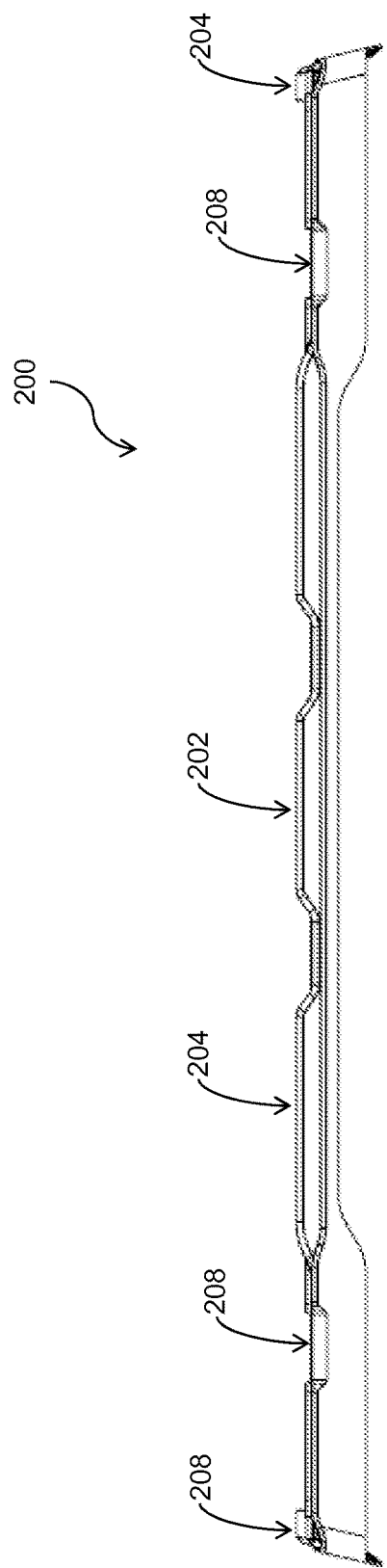
FIG. 15 is a diagram illustrating a side view (along a first side) of a lid.
Figure 16:
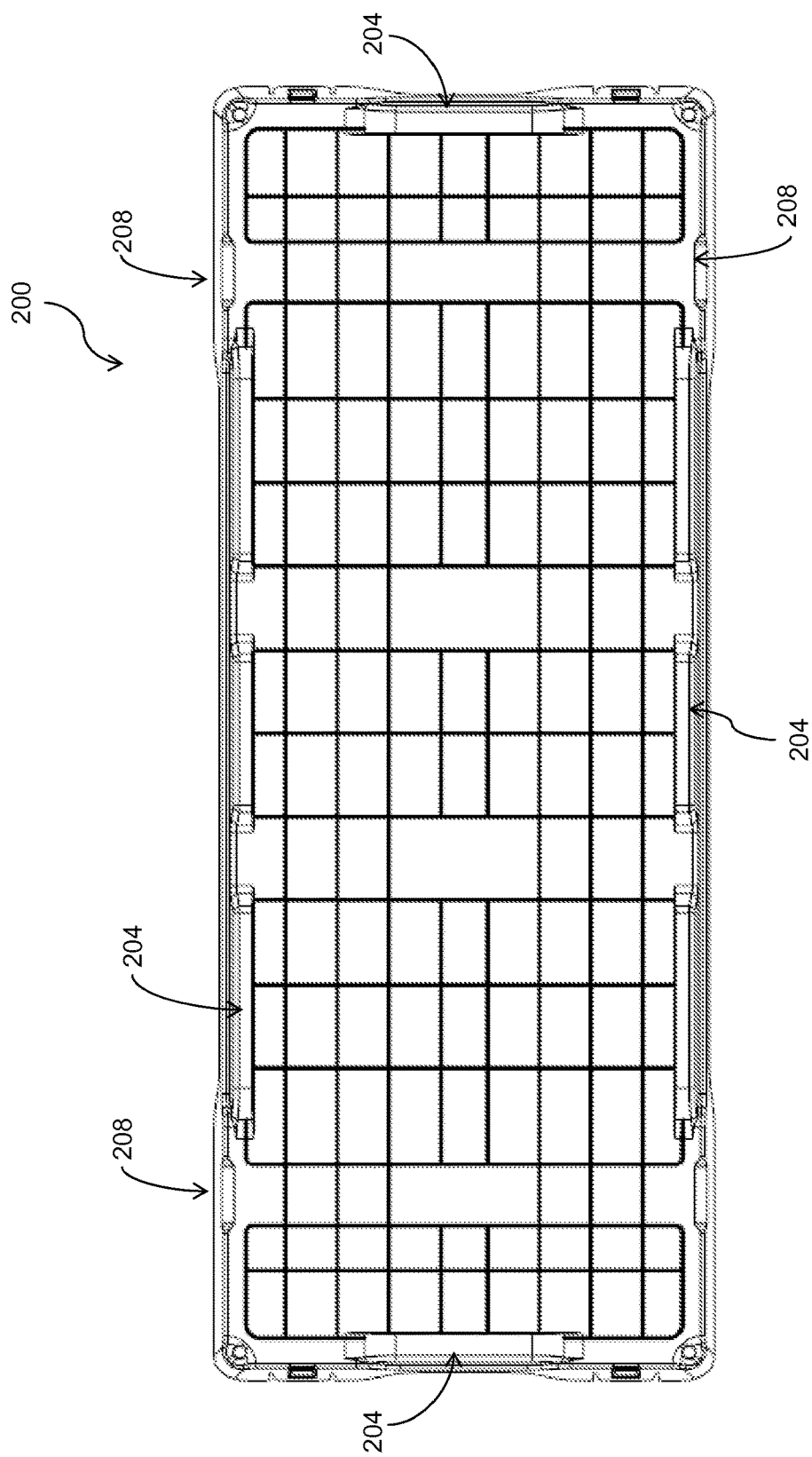
FIG. 16 is a diagram illustrating a bottom view of a lid.
Figure 17:
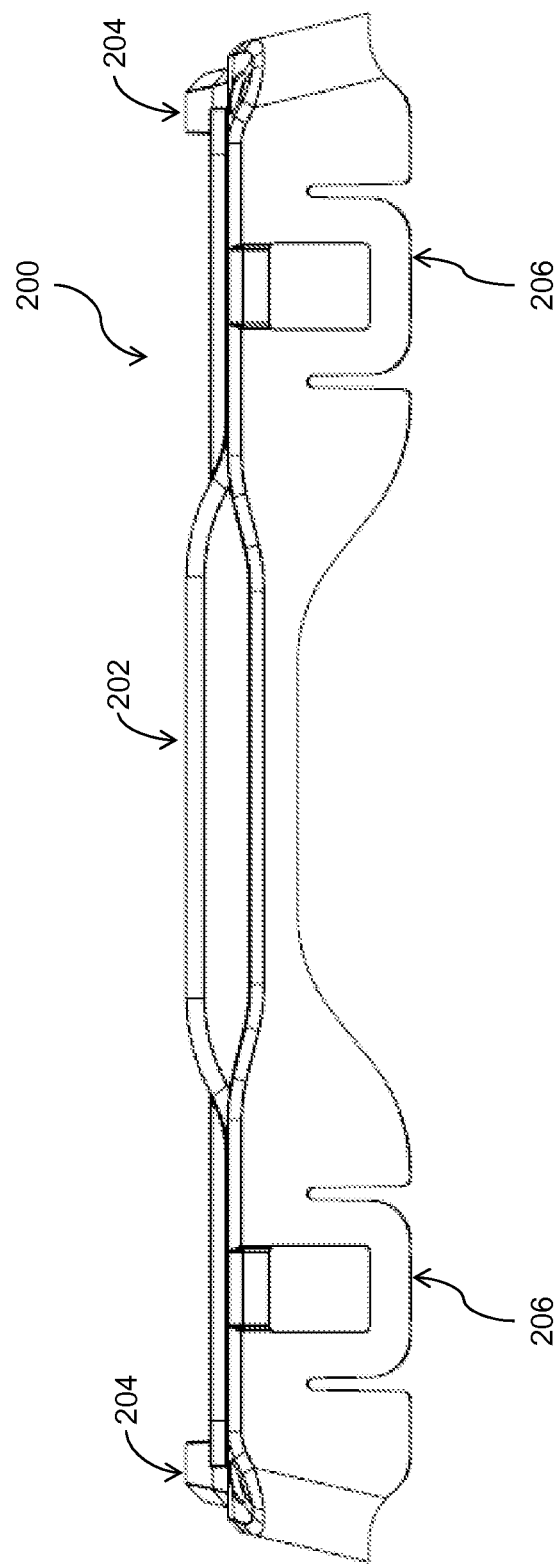
FIG. 17 is a diagram illustrating a side view (along a second side) of a lid.
Figure 18B:
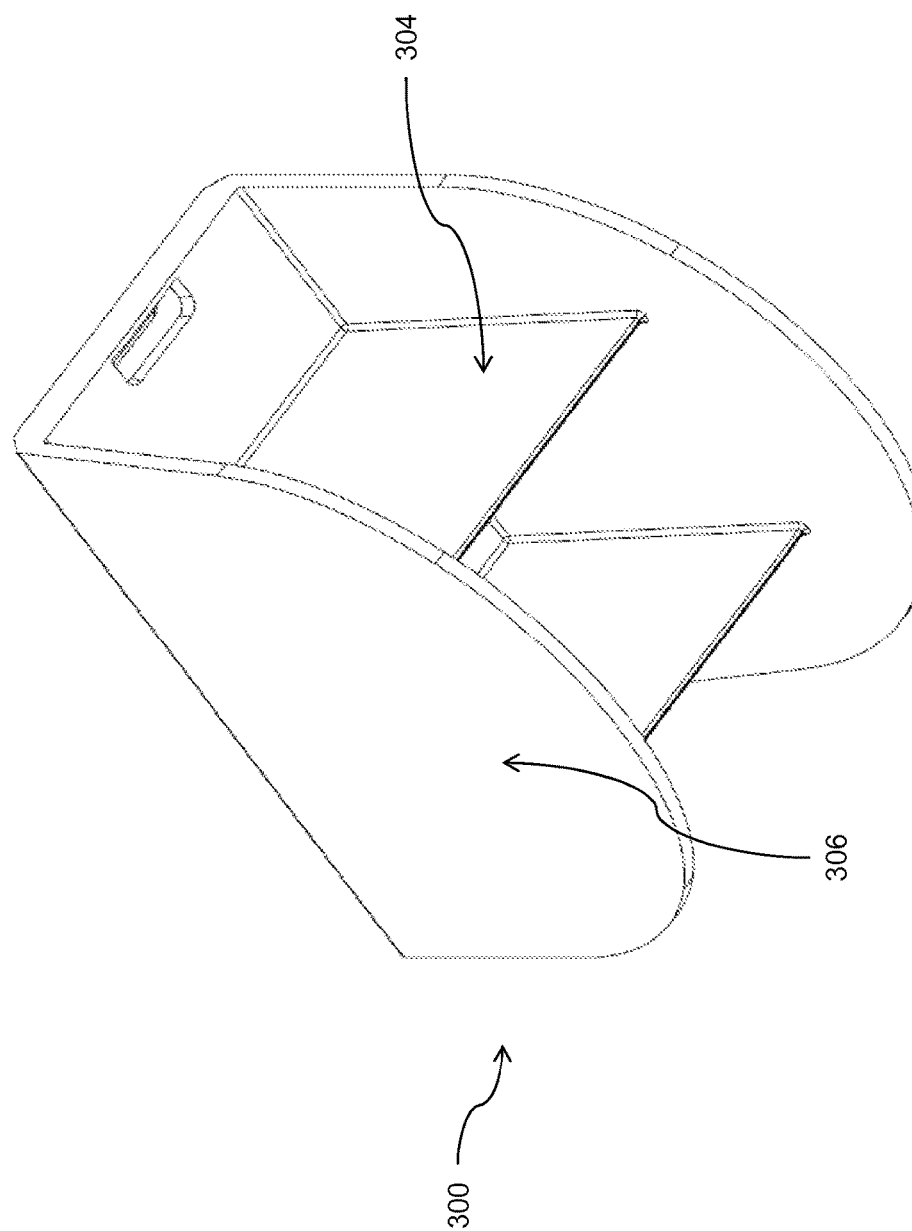
FIGS. 18 a and 18 b are diagrams illustrating various views of a marker arranged to be received within a channel of the core trays of FIGS. 1 to 12.

Reference numerals in the following description represent like (or equivalent) functional and/or structural components or features in the related Figures.

Broadly, the embodiment described herein is a core tray for use in the housing, organisation, transport, cataloguing and storage of core samples. The embodiments described herein are, in some jurisdictions, marketed and sold as the range of CoreSafe™ core trays.

In more detail, referring to FIGS. 1 through 12, there is shown a number of different embodiments of core trays. The embodiments differ in some features and in dimensions, but like numerals are used to denote like features in all Figures.

The core tray 100 depicted in the Figures is made from a plastics material. The plastics material is a UV stabilised plastic, arranged to prevent deterioration of the tray when the tray is placed or left in an outdoor or otherwise exposed environment (e.g. exposed to strong UV light, heat, rain, wind, dust and other environmental factors). It will be understood, however, that the tray may be made from any suitable material. For example, a tray including the features described and defined herein can be made from a metal (such as steel) or even from a wood or wood-like material (e.g. medium-density fibreboard or similar).

Turning to the core tray of FIG. 1, the tray 100 includes a series of channels 102 which are arranged to receive one or more core samples. It will be understood that embodiments of the tray may have one or more channels. The channels are described in more detail later in the specification.

The tray 100 further includes an underside (or bottom) portion 104 which is substantially flat. The substantially flat underside 104 is arranged to allow the tray to be easily moved or slid across a flat surface, such as a table surface, a conveyor line or other such surface.

The tray 100 further includes at least one set of handles 106, arranged to allow a user to easily grip the tray for easy movement, repositioning or carrying of the tray. In particular, it is noted that three different handle arrangements (or variations thereof) are provided, depending on the particular design required for a particular application or requested by a client.

In a first embodiment, the lengths of the handles run along the minor axis or at the "end" of the tray. For the purposes of the embodiment described herein, the trays are of a substantially rectangular shape and generally have a length that is longer than their width. The core sample channels 102, for the purposes of the ensuing description, run parallel to the "length" of the tray. For ease of reference, the specification refers to the length as the "major axis" and the width as the "minor axis". Of course, it will be understood that the broader inventive concept encompasses a "square" tray, where the length and width of the tray are substantively identical. Notwithstanding the dimensions of an embodiment, the terms "length" and "width" are used arbitrarily as mere descriptive aids, and should not be construed as limiting the broader inventive concept.

For example, in one embodiment, the tray has a major axis length of 1000 mm (1 meter) and a minor axis width of 385 mm (38.5 cm). Where reference is made to the minor axis or the "end" of the tray, it will be understood that this generally refers to the side or sides of the tray with the shorter length. That is, to say that the handles are provided on the minor axis or the "ends" of the tray implies that the handles are provided along the sides of the tray that are 385 mm long.

In a second embodiment, handles are provided on the major axis or the "sides" of the tray. Returning to the example given in the previous paragraph, if the minor axis or the "ends" of the tray is defined as the shorter sides of the tray, then it follows that the major axis or the "sides" of the tray are defined as the longer sides of the tray. That is, to say that the handles are provided on the major axis or the "sides" of the tray means that the handles are provided along the sides of the tray that are 1000 mm long. The use of side handles provides a particular advantage, in that a user may more comfortably and easily carry the tray, without needing to bend their wrists into an unnatural position.

It will be understood that the definitions above are provided solely to clarify the relative position of the handles and the terms are not used in a way that limits the broader inventive concepts described herein.

In a third embodiment, handles are provided on both the major and minor axes of the tray. This embodiment provides the maximum amount of flexibility, as it allows the user to correctly grip (and therefore handle) the tray in any number of manners and from almost any position relative to the tray. This embodiment finds particular use in situations where there is little space and it is necessary for the user to be able to handle the tray easily.

It will be further understood that, in the embodiments described above, handles 106 are integrally formed into the edge of tray 100, such that they do not protrude beyond the edge of the tray. Such a feature allows trays to be closely packed together.

Optionally, the tray handles include ribbing 108 so that a user may better grip the handle. The ribbing not only provides better grip but also makes lifting the tray more comfortable as the handle does not "dig" into the user's hands.

Returning to the channels 102, it will be understood that the number of channels provided in the tray are a function of the core sample size that is to be stored in the tray, and also the desired/required length and width of the tray.

For example, where the trays are sized to receive core samples that have been drilled using Boart Longyear's 'Q'™ sized drill bits (a proprietary sizing scheme for drill bits developed and utilised by Boart Longyear), there are provided four different tray types:

"BQ" (36.4 mm) sized tray with 7 channels;
"NQ2" (50.6 mm) sized tray with 5 channels;
"HQ" (63.5 mm) sized tray with 4 channels; and
"PQ" (85 mm) sized tray with 3 channels.

The channels further include a series of spaced apart and different sized ribs 110 which help support the core samples and thereby assist in preventing movement and subsequent damage to the core samples, particularly in situations where the core samples are being loaded or unloaded, or in situations where the core tray is being moved.

Moreover, the ribs 110 serve to "guide" the core sample as it is being inserted into the tray, while simultaneously decreasing the surface area contact between the core sample and the tray, thereby reducing friction and reducing the likelihood of damage or degradation to the core sample.

The channels 102 are arranged to be of a depth where the core is arranged to sit entirely within the channel, such that the core sample sits below the top lip of the tray. This minimises the possibility of damage or interference of the core, particularly where trays are stacked.

At the end of each channel is a finger access recess 112, which allows a user to easily access and grip the end of the core sample, to aid in the removal of the core sample from the channel.

The tray also includes a number of drain holes 114 which are positioned to allow water or fluid to drain from the trays. In situations where no drain facility is required, the tray may be manufactured without drain holes, or alternatively, a small pressure fit plug (not shown) may be utilised to temporarily or permanently plug the drain holes.

A number of other features are incorporated into the design of the trays. The trays include a series of pallet strapping guides 116, which are arranged to allow a series of trays to be strapped together (and/or to a pallet) to facilitate safe movement of the trays.

Moreover, the top lip or edge of the tray 118 and the bottom lip or edge of the tray 120 are of a complementary design, such that when two or more trays are stacked on top of each other, they are designed to "nest", to ensure stability and to also reduce the total shipping height of the nested trays.

Further features incorporated into the trays are arranged to assist in the general handling, cataloguing and storage of the trays. For example, the trays are colour coded. That is, the trays are available in different colours, to assist in tray identification. The colour identification may be used to identify the type of tray, or the contents of the tray, or alternatively, the trays may be provided in high visibility colours for occupational health and safety reasons.

The trays are also arranged such that, where possible, large flat surfaces 122 are presented to the user, which the user can utilise to write notes, attach serial numbers, barcodes, etc., to assist in identification of the trays. In some embodiments the trays include one or more "pre-moulded" bar codes or machine readable indicia (not shown), which may be used to identify each tray individually.

Moreover, the trays further includes at least one tag holder 124 arranged to allow a user to insert a tag. In one embodiment, four tag holders are provided (one on each side of the tray), so that a user can identify the contents of the tray irrespective of the relative orientation of the tray.

Additionally, in one embodiment, trays are manufactured with an embedded RFID (or similar passive or active identification) device (not shown) which allows the trays to be electronically identified. Trays with electronic identification devices find particular use in automated cataloguing or storage facilities, where thousands or tens of thousands of trays are stacked and/or stored within a single facility, or alternatively, where trays are exposed to the elements and conventional labels are likely to be destroyed.

Referring now to FIGS. 13 to 17, there is provided a lid 200 arranged to engage with the core tray depicted generally at FIGS. 1 to 12. The lid includes a ribbed surface 202, wherein the ribbing is arranged to provide additional structural integrity to the lid. It will be understood that in an alternative embodiment, no ribbing is provided.

The lid 200 further includes a series of projections 204 arranged at various locations towards an outer edge of the lid. The projections are arranged to locate within the bottom lip 120 of a core tray 100, such that a core tray can "nest" with the lid 200. In this manner, a core tray 100 with a lid 200 can still nest with other core trays 100, irrespective of whether a lid is utilised.

The lid 200 also includes a series of flexible locking tabs 206, such that the lid may be securely yet removably clipped to a core tray 100. It will be understood that other types of securing mechanisms may be utilised, such as sizing the lid 200 to provide a frictional or pressure fit. Such variations are within the purview of a person skilled in the art.

The lid 200 additionally includes a series of pallet strapping guides 208, which perform the same function as the pallet strapping guides 116 on the core tray 100. That is, they allow a series of core trays with lids to be easily strapped together, by providing a guide which is designed to prevent a securing strap (not shown) from slipping along the edge of the lid. The lid may include a profiled edge (not shown in the Figures) to allow the bottom of one tray to easily slide across the top of the lid, to further assist in stacking the trays.

Referring now to FIGS. 18a to 18f, there is shown a marker 300 arranged to fit within a channel of a core tray. The marker operates to separate or divide core samples within a single channel. The marker includes a top surface 302 which allows a user to write or otherwise mark the surface of the marker 300, or to insert a card. The marker further includes at least one recessed portion 304 (in the Figures shown two complementary recessed portions 304 are shown) arranged to allow a user to grasp the marker 300 and easily insert or remove the marker from the core tray 100. The marker further includes a bridging portion 306, arranged to provide additional structural integrity to the marker 300.

Figure 19:
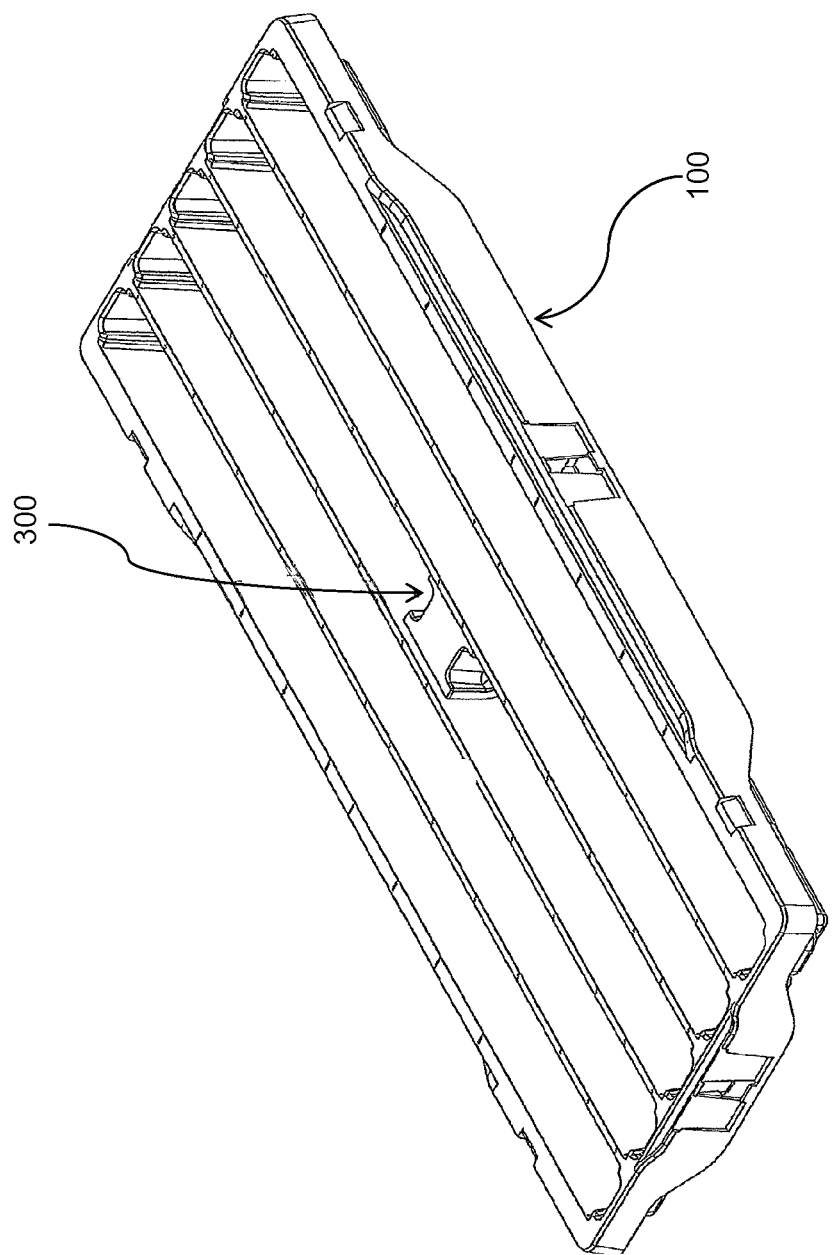
FIG. 19 is a diagram illustrating a perspective view of a core tray including the marker of FIG. 18 in situ.
Figure 20:
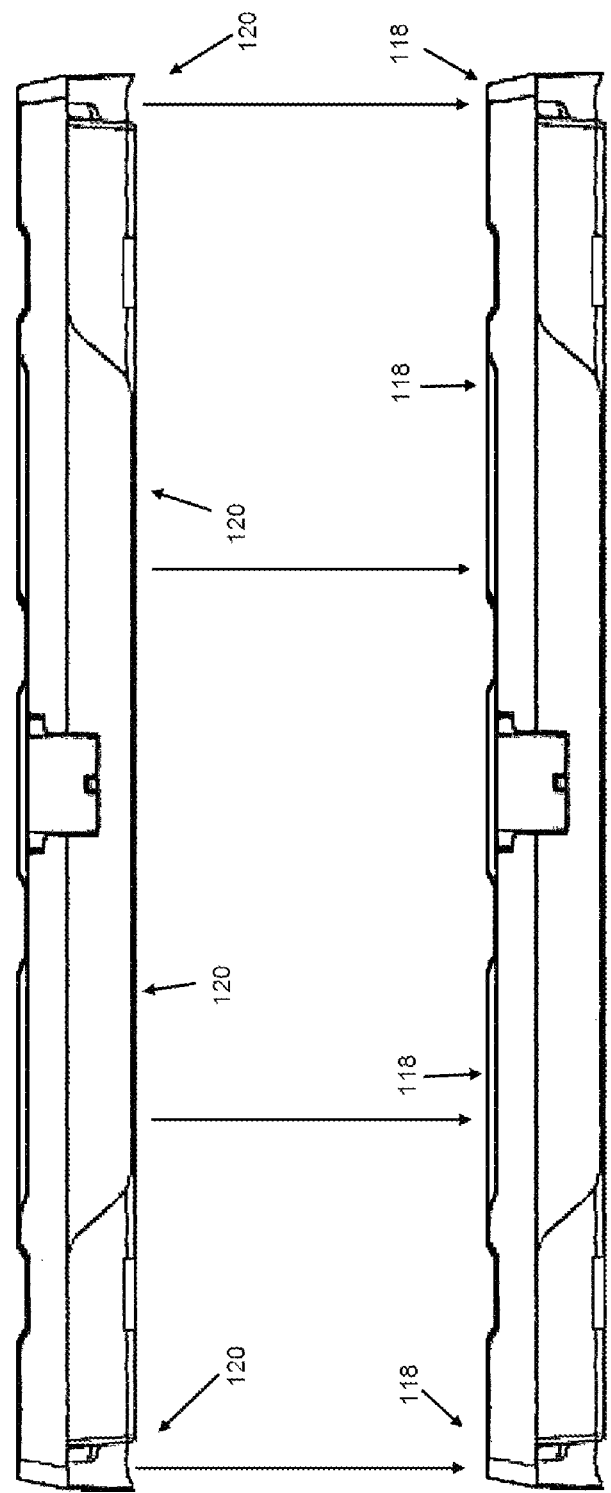
FIG. 20 is a diagram illustrating a side view of a pair of core trays being arranged to stack one on top of another.
Figure 21:
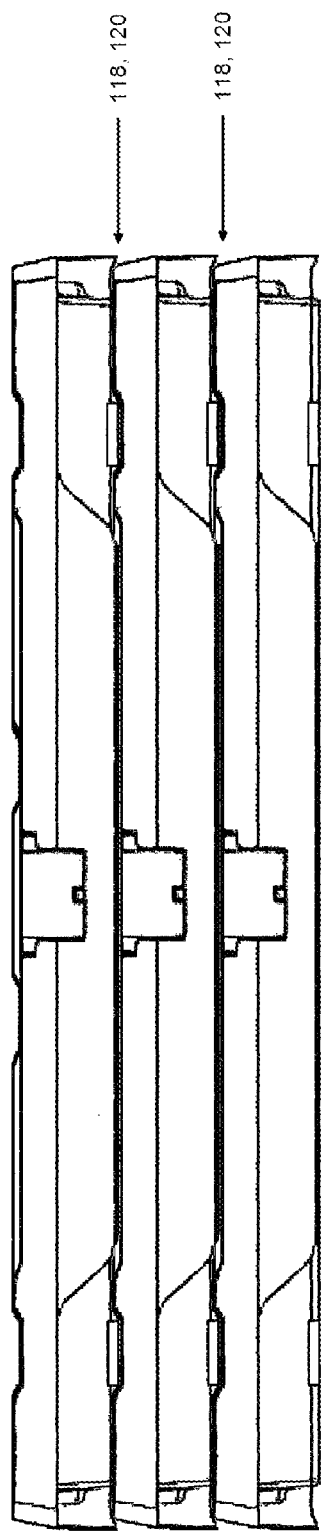
FIG. 21 is a diagram illustrating a stack of three core trays.

As can be seen from FIG. 19, the marker 300 is arranged to sit snugly yet removably within any channel of the core tray 100.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Throughout the specification and claims, unless the context requires otherwise, the word "comprise" or variations such as "comprises" or "comprising", will be understood to imply the inclusion of a stated integer or group of integers but not the exclusion of any other integer or group of integers.

The invention claimed is:

1. A core tray comprising:
   a body including four sides;
   more than one flat-bottomed core sample channel formed in the body shaped to retain at least one core sample;
   a top edge formed on an upper peripheral boundary of said body;
   a base comprising a substantially flat surface formed on an underside of said body, said substantially flat surface enabling the core tray to be slid across a surface;
   a bottom lip extending downwards from a portion of said top edge; and
   a plurality of handles integral to said bottom lip and arranged on all four sides of the core tray body;

wherein said flat-bottomed core sample channels further comprise at least a first and a second guiding rib extending longitudinally along, spaced laterally across and upwardly protruding into said flat-bottomed core sample channels;

said first and second guiding ribs being spaced apart from one another; and said first and second guiding ribs are of different sizes and arranged to inhibit movement, relative to the core tray, of an object supported upon said first and second guiding ribs.

2. The core tray in accordance with claim 1, wherein said plurality of handles extend across two adjacent intersecting sides of the body.

3. The core tray in accordance with claim 1, wherein said plurality of handles comprise a plurality of handle support ribs.

4. The core tray in accordance with claim 1, wherein said flat-bottomed core sample channels further comprise at least one finger access recess located at an end of said at least one channel.

5. The core tray in accordance with claim 1, wherein the flat-bottomed core sample channels include at least one drain hole extending through the base.

6. The core tray in accordance with claim 1, wherein the core tray is integrally formed from a single piece of plastics material.

7. The core tray in accordance with claim 6, wherein the core tray includes at least one identification element integral to said single piece of plastics material.

8. The core tray in accordance with claim 7, wherein said at least one identification element includes a Radio Frequency Identification Device.

9. The core tray in accordance with claim 7, wherein the at least one identification element includes forming the core tray of a specific color of a single piece of plastics material, which is colored to indicate at least one of a type of core tray and a type of the at least one core sample.

10. The core tray in accordance with claim 1 wherein said flat-bottomed core sample channels are shaped to retain a core sample entirely below said top edge of the core tray.

11. The core tray in accordance with claim 1 wherein a first and a second core tray are stackable.

12. The core tray of claim 1 wherein said plurality of handles are arranged in combination of pairs on at least one side of the core tray.

13. The core tray of claim 12 wherein said plurality of handles are located adjacent to a corner of the core tray formed by two adjacent sides.

14. The core tray of claim 1 wherein said plurality of handles are formed as a recess of said bottom lip.

* * * * *